United States Patent
Minor et al.

(10) Patent No.: US 8,058,070 B2
(45) Date of Patent: Nov. 15, 2011

(54) METHOD OF DETERMINING THE COMPONENTS OF A FLUOROOLEFIN COMPOSITION, METHOD OF RECHARGING A FLUID SYSTEM IN RESPONSE THERETO, AND SENSORS USED THEREFOR

(75) Inventors: Barbara Haviland Minor, Elkton, MD (US); Nandini C. Mouli, Reisterstown, MD (US); Daniel B. Laubacher, Wilmington, DE (US); John Carl Steichen, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 677 days.

(21) Appl. No.: 11/855,655

(22) Filed: Sep. 14, 2007

(65) Prior Publication Data
US 2008/0295580 A1 Dec. 4, 2008

Related U.S. Application Data

(60) Provisional application No. 60/844,870, filed on Sep. 15, 2006.

(51) Int. Cl.
*G01N 7/00* (2006.01)
*G01M 3/04* (2006.01)
*G01M 3/00* (2006.01)

(52) U.S. Cl. ............ 436/3; 436/2; 73/40.7; 73/23.2; 73/40; 73/37

(58) Field of Classification Search .......... 436/3, 2; 73/40.7, 40, 37, 23.2
See application file for complete search history.

(56) References Cited

U.S. PATENT DOCUMENTS

| | | | |
|---|---|---|---|
| 5,496,901 A | 3/1996 | DeSimone | |
| 5,996,358 A | 12/1999 | Sumida | |
| 6,170,320 B1 | 1/2001 | Scaringe et al. | |
| 7,022,993 B1* | 4/2006 | Williams et al. | 250/343 |
| 2004/0055317 A1 | 3/2004 | Nomura et al. | |
| 2005/0194560 A1 | 9/2005 | Minor et al. | |
| 2006/0069223 A1 | 3/2006 | Lee et al. | |
| 2006/0130511 A1 | 6/2006 | Brown et al. | |
| 2008/0069177 A1 | 3/2008 | Minor et al. | |
| 2008/0314073 A1* | 12/2008 | Minor | 62/498 |

FOREIGN PATENT DOCUMENTS

| | | |
|---|---|---|
| WO | 00/24843 A | 5/2000 |
| WO | 2005/105947 A | 11/2005 |
| WO | 2006/083022 A | 8/2006 |

(Continued)

OTHER PUBLICATIONS

International Search Report for PCT/US2007/020202, pp. 1-7, Jul. 11, 2008.*

(Continued)

*Primary Examiner* — Christine T Mui

(57) ABSTRACT

Disclosed are a method of determining the components of a fluoroolefin composition, a method of recharging a fluid system in which the composition is used, and sensors used therefor. In particular, the composition may be a fluoroolefin refrigerant composition used within a vapor compression system, where the refrigerant composition is useful in cooling systems as replacements for existing refrigerants with higher global warming potential. Such fluoroolefin refrigerant compositions have double bond structures which make them particularly well suited with sensing technologies, including: infrared sensors, UV/vis sensors, NIR sensors, ion mobility or plasma chromatographs, gas chromatography, refractometry, mass spectroscopy, high temperature thick film sensors, thin film field effect sensors, pellistor sensors, Taguchi sensors and quartz microbalance sensors.

15 Claims, 5 Drawing Sheets

FOREIGN PATENT DOCUMENTS

| WO | 2006094303 A | 9/2006 |
|---|---|---|
| WO | 2007/053697 A | 5/2007 |

OTHER PUBLICATIONS

Non-Final Office Action mailed Mar. 30, 2010, in co-pending U.S. Appl. No. 11/855,621.

Non-Final Office Action mailed Sep. 13, 2010, in co-pending U.S. Appl. No. 11/855,621.

Orkin V L et al: "Rate consstants for the reactions of OH with HFC-245cb (CH3CF2CF3) and some fluoroalkenes (CH2CHCF3, CH2CFCF3, CF2CFCF3, and CF2CF2)" Journal of Physical Chemistry. A, Molecules, Spectroscopy, Kinetics, Environment and General Theory, Washington, DC, US, vol. 101, 1997, pp. 9118-9124, XP 002429691, ISSN: 1089-5639, p. 9122, right hand column; figures 3, 6.

Atkins P W: "Physical Chemistry, Passage" Physical Chemistry, 1990, pp. 458-497, XP002324574, table 16.3.

Communication Relating to the Results of the Partial International Search, 2008.

* cited by examiner

METHOD OF DETERMINING THE COMPONENTS OF A FLUOROOLEFIN COMPOSITION, METHOD OF RECHARGING A FLUID SYSTEM IN RESPONSE THERETO, AND SENSORS USED THEREFOR

CROSS REFERENCE(S) TO RELATED APPLICATION(S)

This application claims the benefit of priority of U.S. Provisional Application 60/844,870, filed Sep. 15, 2006.

FIELD OF THE INVENTION

This disclosure relates to a method of determining the components of a fluoroolefin composition, a method of recharging a fluid system in which the composition is used, and sensors used therefor. In particular, the composition may be a fluoroolefin refrigerant composition used within a vapor compression system. Such refrigerant compositions may be useful in cooling systems as replacements for existing refrigerants with higher global warming potential.

BACKGROUND OF THE INVENTION

New environmental regulations on refrigerants have forced the refrigeration and air-conditioning industry to look for new refrigerants with low global warming potential (GWP).

Replacement refrigerants are being sought that have low GWP, no toxicity, non-flammability, reasonable cost and excellent refrigeration performance.

Fluoroolefins have been proposed as refrigerants alone or in mixtures. When used in a vapor compression system, any refrigerant has a tendency to leak from the system over time, as holes develop in the system. Especially where the refrigerant is a blend of different components, it would be desirable to know the composition of the refrigerant which remains in the system, in order to understand how much of each blend component would be needed to recharge the system. While systems are available for recharging systems which use known refrigerants which are not fluoroolefin based compositions, for instance, as disclosed in US 2004/0055317, to date, no system exists which is particularly useful in identifying the components of fluoroolefin compositions, which may be blends, and in determining the amount of the fluoroolefin components or other components in the blend which need to be added.

SUMMARY OF THE INVENTION

The method of the present invention provides a solution for determining the components of a composition which comprises a fluoroolefin. In addition, the method of the present invention may be used in a fluid system where the system is recharged in response to the determination of the components of the composition.

The method of the present invention is based on the understanding of the unique double bond structure of fluoroolefins. Such double bond structure allows the use of sensing technologies which have heretofore not been available for determining the components of a composition and recharging the composition.

Thus, in accordance with the present invention, there is provided a method of determining the components of a composition comprising a fluoroolefin in a fluid system. The method comprises sensing the components of the composition with sensing means for determining the identity, or the identity and the amount, of the components of the composition. In particular, the sensing means is capable of detecting the double bond structure in the fluoroolefin composition. The method further comprises recharging the components of the composition in response to the determination of the amount of the components of the composition.

Further in accordance with the present invention, there is provided a detection system for determining the identity of the components of a composition comprising a fluoroolefin. Such detection system comprises means for sensing the double bond structure of the fluoroolefin composition. The sensing means may comprise either a sensor which is mounted in-situ in the system, a wand tip which may be used proximate the components of the system, or an extraction device, which may be used remote from the components of the system. The detection system may further include a recovery line disposed between the system and a recharging tank for recharging the components of the composition in response to the amount of the sensed components.

The sensor used in the sensing means of either embodiment may employ any of the following technologies: infrared sensors, UV/vis sensors, NIR sensors, ion mobility or plasma chromatographs, gas chromatography, refractometry, mass spectroscopy, high temperature thick film sensors, thin film field effect sensors, pellistor sensors, Taguchi sensors and quartz microbalance sensors.

DESCRIPTION OF THE INVENTION

Provided in accordance with the present invention is a method of determining the components of a composition comprising a fluoroolefin. Further in accordance with the present invention, there is provided a detection system for detecting the double bond structure in a fluoroolefin composition. Such detection system comprises means for sensing the double bond structure of the fluoroolefin composition.

The fluoroolefin compositions detected with the present invention have a variety of utilities, which include use as foaming agents, blowing agents, fire extinguishing agents, heat transfer mediums (such as heat transfer fluids and refrigerants for use in refrigeration systems, refrigerators, air conditioning systems, heat pumps, chillers, and the like), to name a few. The type of fluid system in which the components of the composition are determined will depend on the utility of the composition. For instance, when the composition is a refrigerant, the fluid system may be a cooling system.

For exemplification, the present invention is illustrated with respect to cooling system of an automotive vehicle. Such a system is shown generally at 10 in FIG. 1. Such a cooling system may be a vapor-compression system. A vapor compression system is a closed loop system which re-uses refrigerant in multiple steps producing a cooling effect in one step and a heating effect in a different step. Such a system generally includes an evaporator, a compressor, a condenser and an expansion device, as will be described below in detail with respect to FIG. 1. The vapor compression system may be used in either stationary or mobile refrigeration or air-conditioning applications.

Figure 1:
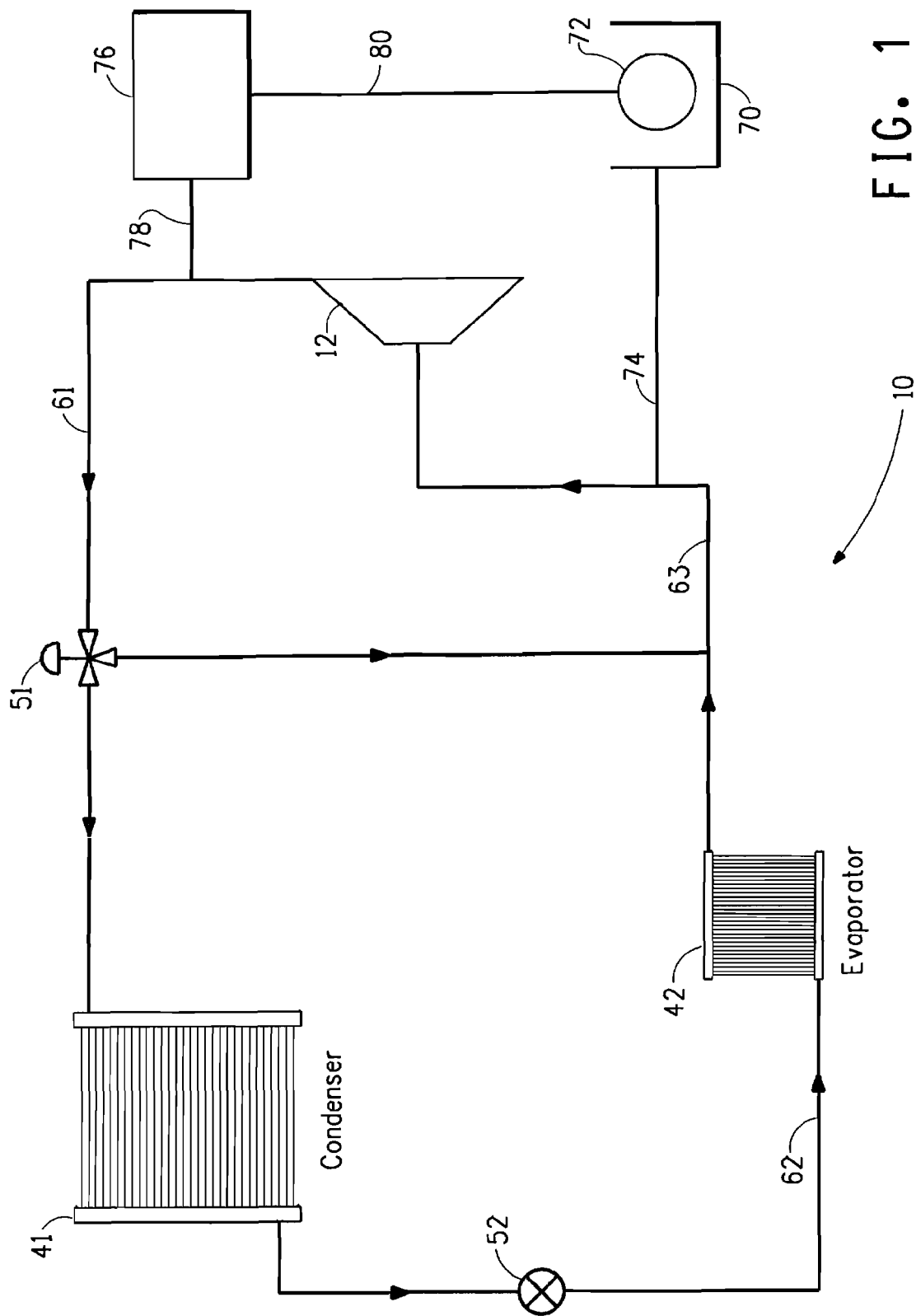
FIG. 1 is a schematic diagram of a refrigeration or air conditioning apparatus, including an extraction device which is used in accordance with the present invention.

With reference to FIG. 1, gaseous refrigerant from an evaporator 42 flows through a hose 63 to the inlet of a compressor 12, and is then discharged. Various types of compressors may be used with the present invention, including reciprocating, rotary, jet, centrifugal, scroll, screw or axial-flow, depending on the mechanical means to compress the fluid, or as positive-displacement (e.g., reciprocating, scroll or screw) or dynamic (e.g., centrifugal or jet).

The compressed refrigerant gas from the compressor flows through the compressor outlet and through a hose 61 to a condenser 41. A pressure regulating valve 51 in hose 61 may be used. This valve allows recycle of the refrigerant flow back to the compressor via a hose 63, thereby providing the ability to control the pressure of the refrigerant reaching the condenser 41 and if necessary to prevent compressor surge. The compressed refrigerant is condensed in the condenser, thus giving off heat. The liquid refrigerant flows through an expansion device 52 via a hose 62 to the evaporator 42, which is located in for instance, the passenger compartment of an automobile, or in the vicinity of another location to be cooled. In the evaporator, the liquid refrigerant is vaporized, providing cooling and the cycle then repeats. The expansion device 52 may be an expansion valve, a capillary tube or an orifice tube.

Figure 1A:
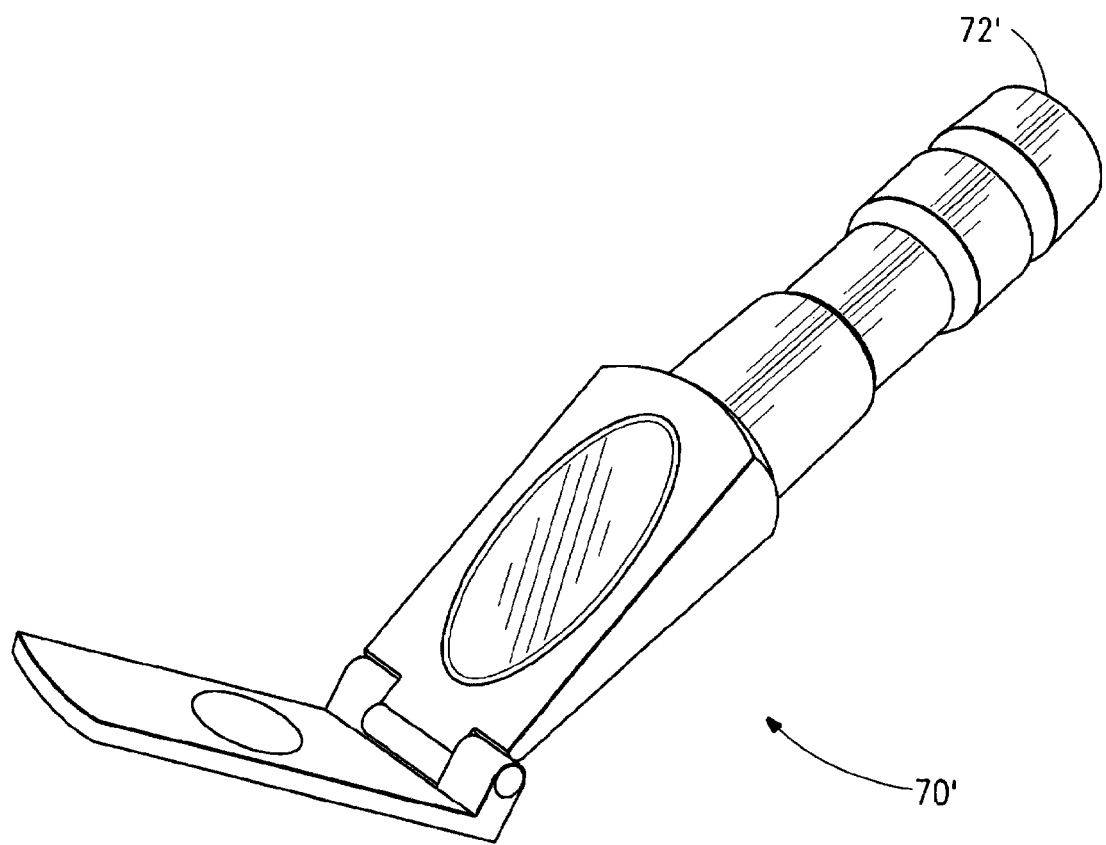
FIG. 1A is a schematic diagram of an example of a wand tip which is used in accordance with the present invention.

In accordance with the present invention, the identity of components of the fluoroolefin composition of the present invention is determined by sensing the components of the composition with sensing means. In addition, the amount of the components of the composition is sensed. The sensing means may include a sensor which is used in-situ in the system. Alternatively, the sensing means may include an extraction device, shown generally at 70 in FIG. 1. A sensor 72 is placed inside the extraction device. A line 74 brings the fluid to be sensed to the extraction device. Alternatively, in another embodiment, the sensing means may comprise a wand tip, as shown at 70' in FIG. 1A. A sensor 72' is included in this hand-held device. This wand tip is generally a hand held device, which may be placed near the fluid in order to determine the components of the composition. An advantage of this type of detector is rapid response so the operator immediately determines the components of the composition as the wand tip passes over the composition. A sensor 72' is included in this hand-held device. The particular device as shown in FIG. 1A is a handheld refractometer for observing liquid samples at atmospheric pressure. However, it should be understood that the present invention is not limited to observing liquid samples, but may also include hand held devices for detecting gases, such as, for example, a hand held gas chromatograph.

The detection system may further include a recovery line disposed between the system and a recharging tank for recharging the components of the composition in response to the amount of the sensed components. Such a recharging tank is shown at 76 in FIG. 1, and the recovery line is shown at 78. The feedback mechanism for recharging the components of the system in response to the amount of the sensed components (80) is disclosed in US 2004/0055317. The detection system of the present invention is particularly useful for recharging a refrigerant blend which contains a volatile component, such as R32. Such component is more likely to leak from the system, and with the present invention, the exact amount of such volatile component may be readily replenished.

The sensor used in the sensing means of either embodiment may employ any of the following technologies: infrared sensors, UV/vis sensors, NIR sensors, ion mobility or plasma chromatographs, gas chromatography, mass spectroscopy, high temperature thick film sensors, thin film field effect sensors, pellistor sensors, Taguchi sensors and quartz microbalance sensors. Such technologies are known in the art.

Infrared sensors of the present invention make use of unique spectral absorbance in the infrared region for all polyatomic gases. By measurement of the spectral intensities in regions specifically selected for a target analyte gas, the concentration of that gas can be determined. There are many techniques available for selecting the spectral region detected including optical filters, spectrographs, transform techniques such as Fourier and Hadamard, emission sources with restricted emission ranges, detectors with specific sensitivities including microphones enclosed with the analyte gas. The application of infrared spectroscopy to gas detection and concentration determination is well known to spectroscopists.

As used herein, UV/vis means "ultraviolet and visible regions of the light spectrum". A UV/vis spectrophotometer measures the intensity of light passing through a sample (I), and compares it to the intensity of light before it passes through the sample ($I_o$). The ratio $I/I_o$ is called the transmittance, and is usually expressed as a percentage (% T). The absorbance A, is based on the transmittance:

$$A = -\log(\% T)$$

The basic parts of a spectrophotometer are a light source (often an incandescent bulb for the visible wavelengths, or a deuterium arc lamp in the ultraviolet), a holder for the sample, a diffraction grating or monochromator to separate the different wavelengths of light, and a detector. The detector is typically a photodiode or a charge-coupled device which stores patterns or charges, commonly known as a CCD. Photodiodes are used with monochromators, which filter the light so that only light of a single wavelength reaches the detector. Diffraction gratings are used with CCD's, which collect light of different wavelengths on different pixels.

As used herein, NIR means "near infrared light spectrum". Near infrared spectrometer (NIRS) is a spectroscopic method utilizing the near infra-red region of the electromagnetic spectrum (from about 800 nm to 2500 nm). NIRS is based on molecular overtone and combination vibrations. The molar absorptivity in the near IR region is typically quite small.

Instrumentation for near-IR spectroscopy is similar to instruments for the visible and mid-IR ranges. There is a source, a detector, and a dispersive element (such as a prism, or more commonly a diffraction grating) to allow the intensity at different wavelengths to be recorded. Fourier transform instruments using an interferometer are also useful, especially for wavelengths above ~1000 nm. Depending on the sample, the spectrum can be measured in transmission or in reflection.

Common incandescent or quartz halogen light bulbs are most often used as broadband sources of near infrared radiation for analytical applications. Light-emitting diodes (LEDs) are also used. The type of detector used depends primarily on the range of wavelengths to be measured. Silicon-based CCDs, InGaAs and PbS devices are suitable.

Ion mobility spectrometry is based upon two principles: (1) the ionization of sample molecules through gas phase chemical reactions by the transfer of an electron or a proton, and (2) the characterization of these ions based upon gas phase mobility in a weak electric field. The mass, size, and shape of these ions will govern the mobility through a voltage gradient, and this can be measured as time required to traverse a fixed distance. Thus IMS detectors yield a drift time or mobility value which is characteristic of certain ions (i.e., chemicals) and provide specificity of response (for example leak detection). The initial step of ion formation is common to all ion mobility spectrometers. In order to achieve this, sample molecules must in some way be transported from a suspected item into the IMS instrument. This is usually accomplished by using a gas pump to sample the air for the suspected leak. Leak detection can be relatively remote from the instrument using a hose (stainless steel or various plastics or rubber) combined with the air-sampling pump. Simultaneous detection of multiple gasses has been demonstrated at the ppm to ppb levels. The ambient air contains a particular reactant ion peak and hydrofluoric acid (HF). The detection by drift time discrimination is shown on the plot of collector current versus drift time. This is a very powerful technique to quickly and unambiguously detect both amounts and composition of the ambient air.

As used herein, GC means is a "gas chromatograph or gas chromatographic analytical technique". Fluids, and refrigerants in particular, can be identified by Micro GC detectors that are ion detectors with varying methods of ionizing the components eluting from the GC's column. An ion detector is analogous to a capacitor or vacuum tube. It can be envisioned as two metal grids separated by air with inverse charges placed on them. An electric potential difference (voltage) exists between the two grids. After components are ionized in the detector, they enter the region between the two grids, causing current to pass from one to the other. This current is amplified and is the signal generated by the detector. The higher the concentration of the component, the more ions are generated, and the greater the current.

A flame ionization detector (FID) uses an air-hydrogen flame to produce ions. As components elute from the GC's column they pass through the flame and are burned, producing ions. The ions produce an electric current, which is the signal output of the detector.

A Thermal Conductivity Detector (TCD) consists of an electrically-heated wire or thermistor. The temperature of the sensing element depends on the thermal conductivity of the gas flowing around it. Changes in thermal conductivity, such as when organic molecules displace some of the carrier gas, cause a temperature rise in the element, which is sensed as a change in resistance.

The Electron Capture Detector (ECD) uses a radioactive Beta particle (electrons) emitter—a typical source contains a metal foil holding 10 millicuries of Nickel-63. The electrons formed are attracted to a positively charged anode, generating a steady current. As the sample is carried into the detector by a stream of nitrogen or a 5% methane, 95% argon mixture, analyte molecules capture the electrons and reduce the current between the collector anode and a cathode. The analyte concentration is thus proportional to the degree of electron capture, and this detector is particularly sensitive to halogens, organometallic compounds, nitrites, or nitro compounds.

The ECD is sensitive with the detection limit of 5 femtograms per second (fg/s), and the detector commonly exhibits a 10,000-fold linear range. This makes it possible to detect the specific halogenated compounds even at levels of only one part per trillion (ppt).

A Photo-Ionization Detector (PID) is an ion detector which uses high-energy photons, typically in the UV range, to produce ions. As components elute from the GC's column they are bombarded by high-energy photons and are ionized. The ions produce an electric current, which is the signal output of the detector. The greater the concentration of the component, the more ions are produced, and the greater the current.

Refractometry uses the Refractive Index of fluids, such as refrigerants, in the liquid state to identify refrigerants in a leak scenario or to determine the composition in a blend so as to adjust to a desired composition. Refractive Index is defined as the angular change in a beam of light passing through the interface of two different substances. The technique uses the fact that each refrigerant has a different atomic composition and therefore a different Refractive Index at a given temperature. Since the Refractive Index is nearly linear with respect of any two components in the mixture, fairly accurate estimates of two or three component mixtures can be made.

A refractometer is used to determine the refractive index of a substance or some physical property of a substance that is directly related to its refractive index. A sample of fluid is introduced into a sample chamber and a source of light is passed through the interface of the fluid and a window in the chamber. The refractometer sensor determines the angle of light emerging from the refrigerant fluid. The fluid is identified by reference to known, pre-determined relationship data for a plurality of different fluids. In a more advanced sensor, the temperature can be varied to obtain data, to identify the constituents of multi-part mixtures of certain fluids and measure the percentage of the mixtures. Certain types of refractometers can be used for measuring gases and liquids.

A traditional handheld refractometer works on the critical angle principle. They utilize lenses and prisms to project a shadow line onto a small glass reticle inside the instrument, which is then viewed by the user through a magnifying eyepiece. In use, a sample is sandwiched between a measuring prism and a small cover plate. Light traveling through the sample is either passed through to the reticle or totally internally reflected. The net effect is that a shadow line is formed between the illuminated area 21 and the dark area. It is at the point that this shadow line crosses the scale that a reading is taken. Because refractive index is very temperature dependent, it is important to use a refractometer with automatic temperature compensation. Compensation is accomplished through the use of a small bi-metal strip that moves a lens or prism in response to temperature changes.

A mass spectrometer is a device that measures the mass-to-charge ratio of ions. This is achieved by ionizing the sample and separating ions of differing masses and recording their relative abundance by measuring intensities of ion flux. A typical mass spectrometer comprises three parts: an ion source, a mass analyzer, and a detector system. Each gas mixture will display a unique spectrum that can be directly related to the composition and concentration of the refrigerant mixture.

The fragmentation patterns of fluoroolefins are unique among fluids, such as other refrigerants and most other environmental gases, allowing it to be specifically identified and its concentration determined relative to other gases present. The fragmentation pattern should be different enough from other gases present near an internal combustion engine such as an automobile engine that it will be easily differentiated by this method. Furthermore, sensing techniques such as mass spectroscopy provide the option of measuring the concentration of other gases that might be present as well.

A gas chromatograph/mass spectrometer sensor uses a gas chromatograph to separate compounds. This stream of separated compounds is fed on-line into the ion source, a metallic filament to which voltage is applied. This filament emits electrons which ionize the compounds. The ions can then further fragment, yielding predictable patterns. Intact ions and fragments pass into the mass spectrometer's analyzer and are eventually detected.

The method of the present invention is particularly useful in determining the components of a fluoroolefin composition and its stereoisomers. In this method, the composition is sensed based on its stereoisomers by the gas chromatograph/mass spectrometer sensor. The stereoisomers of a compound have different boiling points and hence elute at different retention times from the gas chromatograph. This stream of separated compounds is fed on-line into the ion source of a mass spectrometer. The ion source emits electrons which ionize the compounds and the ions can then further fragment based on their mass/charge ratio yielding confirmed patterns for the stereoisomers.

In another embodiment high temperature, thick film sensors may function as sensors for the present inventive method. Many semi-conducting materials become significantly conductive at higher temperatures, e.g., at temperatures above 400° C. These materials become conductive because valence electrons are excited to conduction bands due to their thermal energy. Gases that can either donate or receive electrons from the valence bands change the population of electrons in the conduction bands and thereby the materials conductivity.

Chemical selectivity of high temperature, thick film, sensors is achieved by changing the primary constituent itself and doping the film. In order to impart selectivity to this technique, arrays of sensors containing different primary constituents and/or dopants are employed, and the relationship of the concentration of any given gas to the output of each array-sensing element is determined empirically.

In another embodiment, thin film, field effect sensors may function as sensors for the present inventive method. Field effect sensors are based on the field effect generated by gases in metal oxide semiconductor field-effect transistor (MOSFET) devices with catalytic metals. The charging of the gate contact by the gas molecules results in a voltage change in the sensor signal. The choice of operation temperature, gate metal, and structure of the gate metal determine the selectivity of the gas response. For devices based on silicon (Si) as the semiconductor, Si-MOSFET, the operation temperature is 150-200° C. For devices based on silicon carbide as the semiconductor, SiC-MOSFET, the operation temperature is 200-600° C.

The selectivity and sensitivity of MOSFET sensors is achieved by modification of the semiconductor, its doping, and the temperature at which the device is operated.

In another embodiment, pellistor catalytic gas sensors may be used as sensors in the present inventive method. The pellistor is a miniature calorimeter used to measure the energy liberated on oxidation of a gas. It consists of a coil of small diameter platinum wire supported in a refractory bead. The coil is used to heat the bead electrically to its operating temperature (about 500° C.) and to detect changes in temperature produced by the oxidation of the gas. Selectivity of pellistor sensors is achieved by modification of the composition of the refractory bead.

In another embodiment, Taguchi sensors may be used as sensors in the present inventive method. Taguchi sensors are composed of powders made of semiconducting metal oxides. When a metal oxide crystal such as $SnO_2$ is heated at a certain high temperature in air, oxygen is adsorbed on the crystal surface with a negative charge. Then donor electrons in the crystal surface are transferred to the adsorbed oxygen, resulting in leaving positive charges in a space charge layer. Thus, surface potential is formed to serve as a potential barrier against electron flow. Inside the sensor, electric current flows through the conjunction parts (grain boundary) of $SnO_2$ micro crystals. At grain boundaries, adsorbed oxygen forms a potential barrier that prevents carriers from moving freely. The electrical resistance of the sensor is attributed to this potential barrier.

In the presence of gases capable of removing oxygen from the surface at high temperature, the surface density of the negatively charged oxygen decreases, so the barrier height in the grain boundary is reduced. The reduced barrier height decreases sensor resistance.

The selectivity and sensitivity of Taguchi sensors can be modified through selection of the metal oxides, oxide doping, and other modifications of the oxide surface along with the temperature of operation.

In another embodiment, Quartz Microbalance Sensors may be used as sensors in the present inventive method. Quartz microbalance sensor technology is based on measuring the frequency of polymer-coated quartz crystals. The frequency is influenced by bulk absorption of analyte molecules into the polymer matrix. The sensitivity and selectivity of the microbalance sensors can be varied through the selection of different polymer coatings, having different functional groups in the side chains. Bulk absorption of analyte molecules into the polymer layer increases the mass of the quartz crystal, resulting in a decrease of the resonance frequency. The absorption process is fully reversible. Resins, such as those sold under the trademark Nafion® by E.I. du Pont de Nemours and Company of Wilmington, Del., PTFE, and polystyrene sulfonates are used to tailor the sensor response to specific analytes including refrigerant gases.

These sensing technologies have been found to be particularly useful in determining the components of fluoroolefin compositions, which have double bonds. Representative fluoroolefins include but are not limited to all compounds as listed in Table 1 and Table 2. As can be seen to from these Tables, the fluoroolefins have at least one double bond.

Fluoroolefins comprise compounds with 2 to 12 carbon atoms, in another embodiment 3 to 10 carbon atoms, and in yet another embodiment 3 to 7 carbon atoms. In one embodiment of the invention fluoroolefins may be compounds (and mixtures of such compounds) having the formula E- or Z—$R^1CH=CHR^2$ (Formula I), wherein $R^1$ and $R^2$ are, independently, $C_1$ to $C_6$ perfluoroalkyl groups. Examples of $R^1$ and $R^2$ groups include, but are not limited to, $CF_3$, $C_2F_5$, $CF_2CF_2CF_3$, $CF(CF_3)_2$, $CF_2CF_2CF_2CF_3$, $CF(CF_3)CF_2CF_3$, $CF_2CF(CF_3)_2$, $C(CF_3)_3$, $CF_2CF_2CF_2CF_2CF_3$, $CF_2CF_2CF(CF_3)_2$, $C(CF_3)_2C_2F_5$, $CF_2CF_2CF_2CF_2CF_2CF_3$, $CF(CF_3)CF_2CF_2C_2F_5$, and $C(CF_3)_2CF_2C_2F_5$. Exemplary, non-limiting Formula I compounds are presented in Table 1.

TABLE 1

| Code | Structure | Chemical Name |
|---|---|---|
| F11E | $CF_3CH=CHCF_3$ | 1,1,1,4,4,4-hexafluorobut-2-ene |
| F12E | $CF_3CH=CHC_2F_5$ | 1,1,1,4,4,5,5,5-octafluoropent-2-ene |
| F13E | $CF_3CH=CHCF_2C_2F_5$ | 1,1,1,4,4,5,5,6,6,6-decafluorohex-2-ene |
| F13iE | $CF_3CH=CHCF(CF_3)_2$ | 1,1,1,4,5,5,5-heptafluoro-4-(trifluoromethyl)pent-2-ene |

TABLE 1-continued

| Code | Structure | Chemical Name |
|---|---|---|
| F22E | $C_2F_5CH=CHC_2F_5$ | 1,1,1,2,2,5,6,6,6-decafluorohex-3-ene |
| F14E | $CF_3CH=CH(CF_2)_3CF_3$ | 1,1,1,4,4,5,5,6,6,7,7,7-dodecafluorohept-2-ene |
| F14iE | $CF_3CH=CHCF_2CF-(CF_3)_2$ | 1,1,1,4,4,5,6,6,6-nonafluoro-5-(trifluoromethyl)hex-2-ene |
| F14sE | $CF_3CH=CHCF(CF_3)-C_2F_5$ | 1,1,1,4,5,5,6,6,6-nonfluoro-4-(trifluoromethyl)hex-2-ene |
| F14tE | $CF_3CH=CHC(CF_3)_3$ | 1,1,1,5,5,5-hexafluoro-4,4-bis(trifluoromethyl)pent-2-ene |
| F23E | $C_2F_5CH=CHCF_2C_2F_5$ | 1,1,1,2,2,5,5,6,6,7,7,7-dodecafluorohept-3-ene |
| F23iE | $C_2F_5CH=CHCF(CF_3)_2$ | 1,1,1,2,2,5,6,6,6-nonafluoro-5-(trifluoromethyl)hex-3-ene |
| F15E | $CF_3CH=CH(CF_2)_4CF_3$ | 1,1,1,4,4,5,5,6,6,7,8,8,8-tetradecafluorooct-2-ene |
| F15iE | $CF_3CH=CH-CF_2CF_2CF(CF_3)_2$ | 1,1,1,4,4,5,5,6,7,7,7-undecafluoro-6-(trifluoromethyl)hept-2-ene |
| F15tE | $CF_3CH=CH-C(CF_3)_2C_2F_5$ | 1,1,1,5,5,6,6,6-octafluoro-4,4-bis(trifluoromethyl)hex-2-ene |
| F24E | $C_2F_5CH=CH(CF_2)_3CF_3$ | 1,1,1,2,2,5,5,6,6,7,7,8,8,8-tetradecafluorooct-3-ene |
| F24iE | $C_2F_5CH=CHCF_2CF-(CF_3)_2$ | 1,1,1,2,2,5,5,6,7,7,7-undecafluoro-6-(trifluoromethyl)hept-3-ene |
| F24sE | $C_2F_5CH=CHCF(CF_3)-C_2F_5$ | 1,1,1,2,2,5,6,6,7,7,7-undecafluoro-5-(trifluoromethyl)hept-3-ene |
| F24tE | $C_2F_5CH=CHC(CF_3)_3$ | 1,1,1,2,2,6,6,6-octafluoro-5,5-bis(trifluoromethyl)hex-3-ene |
| F33E | $C_2F_5CF_2CH=CH-CF_2C_2F_5$ | 1,1,1,2,2,3,3,6,6,7,7,8,8,8-tetradecafluorooct-4-ene |
| F3i3iE | $(CF_3)_2CFCH=CH-CF(CF_3)_2$ | 1,1,1,2,5,6,6,6-octafluoro-2,5-bis(trifluoromethyl)hex-3-ene |
| F33iE | $C_2F_5CF_2CH=CH-CF(CF_3)_2$ | 1,1,1,2,5,5,6,6,7,7,7-undecafluoro-2-(trifluoromethyl)hept-3-ene |
| F16E | $CF_3CH=CH(CF_2)_5CF_3$ | 1,1,1,4,4,5,5,6,6,7,7,8,8,,9,9,9-hexadecafluoronon-2-ene |
| F16sE | $CF_3CH=CHCF(CF_3)(CF_2)_2C_2F_5$ | 1,1,1,4,5,5,6,6,7,7,8,8,8-tridecafluoro-4-(trifluoromethyl)hept-2-ene |
| F16tE | $CF_3CH=CHC(CF_3)_2CF_2C_2F_5$ | 1,1,1,6,6,6-octafluoro-4,4-bis(trifluoromethyl)hept-2-ene |
| F25E | $C_2F_5CH=CH(CF_2)_4CF_3$ | 1,1,1,2,2,5,5,6,6,7,7,8,8,9,9,9-hexadecafluoronon-3-ene |
| F25iE | $C_2F_5CH=CH-CF_2CF_2CF(CF_3)_2$ | 1,1,1,2,2,5,5,6,6,7,8,8,8-tridecafluoro-7-(trifluoromethyl)oct-3-ene |
| F25tE | $C_2F_5CH=CH-C(CF_3)_2C_2F_5$ | 1,1,1,2,2,6,6,7,7,7-decafluoro-5,5-bis(trifluoromethyl)hept-3-ene |
| F34E | $C_2F_5CF_2CH=CH-(CF_2)_3CF_3$ | 1,1,1,2,2,3,3,6,6,7,7,8,8,9,9,9-hexadecafluoronon-4-ene |
| F34iE | $C_2F_5CF_2CH=CH-CF_2CF(CF_3)_2$ | 1,1,1,2,2,3,3,6,6,7,8,8,8-tridecafluoro-7-(trifluoromethyl)oct-4-ene |
| F34sE | $C_2F_5CF_2CH=CH-CF(CF_3)C_2F_5$ | 1,1,1,2,2,3,3,6,7,7,8,8,8-tridecafluoro-6-(trifluoromethyl)oct-4-ene |
| F34tE | $C_2F_5CF_2CH=CH-C(CF_3)_3$ | 1,1,1,5,5,6,6,7,7,7-decafluoro-2,2-bis(trifluoromethyl)hept-3-ene |
| F3i4E | $(CF_3)_2CFCH=CH-(CF_2)_3CF_3$ | 1,1,1,2,5,5,6,6,7,7,8,8,8-tridecafluoro-2(trifluoromethyl)oct-3-ene |
| F3i4iE | $(CF_3)_2CFCH=CH-CF_2CF(CF_3)_2$ | 1,1,1,2,5,5,6,7,7,7-decafluoro-2,6-bis(trifluoromethyl)hept-3-ene |
| F3i4sE | $(CF_3)_2CFCH=CH-CF(CF_3)C_2F_5$ | 1,1,1,2,5,6,6,7,7,7-decafluoro-2,5-bis(trifluoromethyl)hept-3-ene |
| F3i4tE | $(CF_3)_2CFCH=CH-C(CF_3)_3$ | 1,1,1,2,6,6,6-heptafluoro-2,5,5-tris(trifluoromethyl)hex-3-ene |
| F26E | $C_2F_5CH=CH(CF_2)_5CF_3$ | 1,1,1,2,2,5,5,6,6,7,7,8,8,9,9,10,10,10-octadecafluorodec-3-ene |
| F26sE | $C_2F_5CH=CHCF(CF_3)(CF_2)_2C_2F_5$ | 1,1,1,2,2,5,5,6,6,7,7,8,8,9,9,9-pentadecafluoro-5-(trifluoromethyl)non-3-ene |
| F26tE | $C_2F_5CH=CHC(CF_3)_2CF_2C_2F_5$ | 1,1,1,2,2,6,6,7,7,8,8,8-dodecafluoro-5,5-bis(trifluoromethyl)oct-3-ene |
| F35E | $C_2F_5CF_2CH=CH-(CF_2)_4CF_3$ | 1,1,1,2,2,3,3,6,6,7,7,8,8,9,9,10,10,10-octadecafluorodec-4-ene |
| F35iE | $C_2F_5CF_2CH=CH-CF_2CF_2CF(CF_3)_2$ | 1,1,1,2,2,3,3,6,6,7,7,8,9,9,9-pentadecafluoro-8-(trifluoromethyl)non-4-ene |
| F35tE | $C_2F_5CF_2CH=CH-C(CF_3)_2C_2F_5$ | 1,1,1,2,2,3,3,7,7,8,8,8-dodecafluoro-6,6-bis(trifluoromethyl)oct-4-ene |
| F3i5E | $(CF_3)_2CFCH=CH-C(CF_2)_4CF_3$ | 1,1,1,2,5,5,6,6,7,7,8,8,9,9,9-pentadecafluoro-2-(trifluoromethyl)non-3-ene |
| F3i5iE | $(CF_3)_2CFCH=CH-CF_2CF_2CF(CF_3)_2$ | 1,1,1,2,5,5,6,6,7,8,8,8-dodecafluoro-2,7-bis(trifluoromethyl)oct-3-ene |
| F3i5tE | $(CF_3)_2CFCH=CH-C(CF_3)_2C_2F_5$ | 1,1,1,2,6,6,6,7,7,7-nonafluoro-2,5,5-tris(trifluoromethyl)hept-3-ene |
| F44E | $CF_3(CF_2)_3CH=CH-(CF_2)_3CF_3$ | 1,1,1,2,2,3,3,4,4,7,7,8,8,9,9,10,10,10-octadecafluorodec-5-ene |
| F44iE | $CF_3(CF_2)_3CH=CH-CF_2CF(CF_3)_2$ | 1,1,1,2,3,3,6,6,7,7,8,8,9,9,9-pentadecafluoro-2-(trifluoromethyl)non-4-ene |
| F44sE | $CF_3(CF_2)_3CH=CH-CF(CF_3)C_2F_5$ | 1,1,1,2,2,3,6,6,7,7,8,8,9,9,9-pentadecafluoro-3-(trifluoromethyl)non-4-ene |
| F44tE | $CF_3(CF_2)_3CH=CH-C(CF_3)_3$ | 1,1,1,5,5,6,6,7,7,8,8,8-dodecafluoro-2,2,-bis(trifluoromethyl)oct-3-ene |
| F4i4iE | $(CF_3)_2CFCF_2CH=CH-CF_2CF(CF_3)_2$ | 1,1,1,2,3,3,6,6,7,7,8,8,8-dodecafluoro-2,7-bis(trifluoromethyl)oct-4-ene |
| F4i4sE | $(CF_3)_2CFCF_2CH=CH-CF(CF_3)C_2F_5$ | 1,1,1,2,3,3,6,7,7,8,8,8-dodecafluoro-2,6-bis(trifluoromethyl)oct-4-ene |
| F4i4tE | $(CF_3)_2CFCF_2CH=CH-C(CF_3)_3$ | 1,1,1,5,5,6,7,7,7-nonafluoro-2,2,6-tris(trifluoromethyl)hept-3-ene |
| F4s4sE | $C_2F_5CF(CF_3)CH=CH-CF(CF_3)C_2F_5$ | 1,1,1,2,2,3,6,7,7,8,8,8-dodecafluoro-3,6-bis(trifluoromethyl)oct-4-ene |
| F4s4tE | $C_2F_5CF(CF_3)CH=CH-C(CF_3)_3$ | 1,1,1,5,6,6,7,7,7-nonafluoro-2,2,5-tris(trifluoromethyl)hept-3-ene |
| F4t4tE | $(CF_3)_3CCH=CH-C(CF_3)_3$ | 1,1,1,6,6,6-hexafluoro-2,2,5,5-tetrakis(trifluoromethyl)hex-3-ene |

Compounds of Formula I may be prepared by contacting a perfluoroalkyl iodide of the formula $R^1I$ with a perfluoroalkyltrihydroolefin of the formula $R^2CH=CH_2$ to form a trihydroiodoperfluoroalkane of the formula $R^1CH_2CHIR^2$. This trihydroiodoperfluoroalkane can then be dehydroiodinated to form $R^1CH=CHR^2$. Alternatively, the olefin $R^1CH=CHR^2$ may be prepared by dehydroiodination of a trihydroiodoperfluoroalkane of the formula $R^1CHICH_2R^2$ formed in turn by reacting a perfluoroalkyl iodide of the formula $R^2I$ with a perfluoroalkyltrihydroolefin of the formula $R^1CH=CH_2$. This contacting of a perfluoroalkyl iodide with a perfluoroalkyltrihydroolefin may take place in batch mode by combining the reactants in a suitable reaction vessel capable of operating under the autogenous pressure of the reactants and products at reaction temperature. Suitable reaction vessels include fabricated from stainless steels, in particular of the austenitic type, and the well-known high nickel alloys such as nickel-copper alloys sold under the trademark Monel®, Hastelloy® nickel based alloys sold under the trademark Hastelloy® and nickel-chromium alloys sold under the trademark Inconel®.

Alternatively, the reaction may take be conducted in semi-batch mode in which the perfluoroalkyltrihydroolefin reactant is added to the perfluoroalkyl iodide reactant by means of a suitable addition apparatus such as a pump at the reaction temperature. The ratio of perfluoroalkyl iodide to perfluoroalkyltrihydroolefin should be between about 1:1 to about 4:1, preferably from about 1.5:1 to 2.5:1. Ratios less than 1.5:1 tend to result in large amounts of the 2:1 adduct as reported by Jeanneaux, et. al. in Journal of Fluorine Chemistry, Vol. 4, pages 261-270 (1974).

In some embodiments, temperatures for contacting of said perfluoroalkyl iodide with said perfluoroalkyltrihydroolefin are preferably within the range of about 150° C. to 300° C., preferably from about 170° C. to about 250° C., and most preferably from about 180° C. to about 230° C. Suitable contact times for the reaction of the perfluoroalkyl iodide with the perfluoroalkyltrihydroolefin are from about 0.5 hour to 18 hours, preferably from about 4 to about 12 hours.

The trihydroiodoperfluoroalkane prepared by reaction of the perfluoroalkyl iodide with the perfluoroalkyltrihydroolefin may be used directly in the dehydroiodination step or in some embodiments be is recovered and purified by distillation prior to the dehydroiodination step.

In some embodiments, the dehydroiodination step is carried out by contacting the trihydroiodoperfluoroalkane with a basic substance. Suitable basic substances include alkali metal hydroxides (e.g., sodium hydroxide or potassium hydroxide), alkali metal oxide (for example, sodium oxide), alkaline earth metal hydroxides (e.g., calcium hydroxide), alkaline earth metal oxides (e.g., calcium oxide), alkali metal alkoxides (e.g., sodium methoxide or sodium ethoxide), aqueous ammonia, sodium amide, or mixtures of basic substances such as soda lime. Preferred basic substances are sodium hydroxide and potassium hydroxide. Said contacting of the trihydroiodoperfluoroalkane with a basic substance may take place in the liquid phase preferably in the presence of a solvent capable of dissolving at least a portion of both reactants. Solvents suitable for the dehydroiodination step include one or more polar organic solvents such as alcohols (e.g., methanol, ethanol, n-propanol, isopropanol, n-butanol, isobutanol, and tertiary butanol), nitrites (e.g., acetonitrile, propionitrile, butyronitrile, benzonitrile, or adiponitrile), dimethyl sulfoxide, N,N-dimethylformamide, N,N-dimethylacetamide, or sulfolane. The choice of solvent may depend on the boiling point product and the ease of separation of traces of the solvent from the product during purification. Typically, ethanol or isopropanol are good solvents for the reaction.

In some embodiments, the dehydroiodination reaction may be carried out by addition of one of the reactants (either the basic substance or the trihydroiodoperfluoroalkane) to the other reactant in a suitable reaction vessel. Said reaction may be fabricated from glass, ceramic, or metal and is preferably agitated with an impeller or stirring mechanism.

In certain embodiments, the temperatures suitable for the dehydroiodination reaction are from about 10° C. to about 100° C., preferably from about 20° C. to about 70° C. In other embodiments, the dehydroiodination reaction may be carried out at ambient pressure or at reduced or elevated pressure. In certain embodiments, dehydroiodination reactions is one in which the compounds of Formula I is distilled out of the reaction vessel as it is formed.

In alternative embodiments, the dehydroiodination reaction may be conducted by contacting an aqueous solution of said basic substance with a solution of the trihydroiodoperfluoroalkane in one or more organic solvents of lower polarity such as an alkane (e.g., hexane, heptane, or octane), aromatic hydrocarbon (e.g., toluene), halogenated hydrocarbon (e.g., methylene chloride, chloroform, carbon tetrachloride, or perchloroethylene), or ether (e.g., diethyl ether, methyl tert-butyl ether, tetrahydrofuran, 2-methyl tetrahydrofuran, dioxane, dimethoxyethane, diglyme, or tetraglyme) in the presence of a phase transfer catalyst. Suitable phase transfer catalysts include quaternary ammonium halides (e.g., tetrabutylammonium bromide, tetrabutylammonium hydrosulfate, triethylbenzylammonium chloride, dodecyltrimethylammonium chloride, and tricaprylylmethylammonium chloride), quaternary phosphonium halides (e.g., triphenylmethylphosphonium bromide and tetraphenylphosphonium chloride), or cyclic polyether compounds known in the art as crown ethers (e.g., 18-crown-6 and 15-crown-5).

According to alternative embodiments, the dehydroiodination reaction may be conducted in the absence of solvent by adding the trihydroiodoperfluoroalkane to a solid or liquid basic substance.

In some embodiments, suitable reaction times for the dehydroiodination reactions are from about 15 minutes to about six hours or more depending on the solubility of the reactants. In some embodiments, the dehydroiodination reaction is rapid and requires about 30 minutes to about three hours for completion.

The compound of Formula I may be recovered from the dehydroiodination reaction mixture by phase separation after addition of water, by distillation, or by a combination thereof.

The compositions in some embodiments may comprise a single compound of Formula I, for example, one of the compounds in Table 1, or may comprise a combination of compounds of Formula I.

In another embodiment, fluoroolefins may be compounds as presented in Table 2 (including mixtures thereof). The compositions in some embodiment may comprise a single compound in Table 2, or may comprise a combination of compounds of Table 2.

TABLE 2

| Code | Structure | Chemical name |
| --- | --- | --- |
| HFC-1225ye | $CF_3CF=CHF$ | 1,2,3,3,3-pentafluoro-1-propene |
| HFC-1225zc | $CF_3CH=CF_2$ | 1,1,3,3,3-pentafluoro-1-propene |
| HFC-1225yc | $CHF_2CF=CF_2$ | 1,1,2,3,3-pentafluoro-1-propene |
| HFC-1234ye | $CHF_2CF=CHF$ | 1,2,3,3-tetrafluoro-1-propene |
| HFC-1234yf | $CF_3CF=CH_2$ | 2,3,3,3-tetrafluoro-1-propene |
| HFC-1234ze | $CF_3CH=CHF$ | 1,3,3,3-tetrafluoro-1-propene |
| HFC-1234yc | $CH_2FCF=CF_2$ | 1,1,2,3-tetrafluoro-1-propene |
| HFC-1234zc | $CHF_2CH=CF_2$ | 1,1,3,3-tetrafluoro-1-propene |

TABLE 2-continued

| Code | Structure | Chemical name |
|---|---|---|
| HFC-1234ye | $CHF_2CF=CHF$ | 1,2,3,3-tetrafluoro-1-propene |
| HFC-1243yf | $CHF_2CF=CH_2$ | 2,3,3-trifluoro-1-propene |
| HFC-1243zf | $CF_3CH=CH_2$ | 3,3,3-trifluoro-1-propene |
| HFC-1243yc | $CH_3CF=CF_2$ | 1,1,2-trifluoro-1-propene |
| HFC-1243zc | $CH_2FCH=CF_2$ | 1,1,3-trifluoro-1-propene |
| HFC-1243ye | $CHF_2CF=CHF$ | 1,2,3-trifluoro-1-propene |
| HFC-1243ze | $CHF_2CH=CHF$ | 1,3,3-trifluoro-1-propene |
| FC-1318my | $CF_3CF=CFCF_3$ | 1,1,1,2,3,4,4,4-octafluoro-2-butene |
| FC-1318cy | $CF_3CF_2CF=CF_2$ | 1,1,2,3,3,4,4,4-octafluoro-1-butene |
| HFC-1327my | $CF_3CF=CHCF_3$ | 1,1,1,2,4,4,4-heptafluoro-2-butene |
| HFC-1327ye | $CHF=CFCF_2CF_3$ | 1,2,3,3,4,4,4-heptafluoro-1-butene |
| HFC-1327py | $CHF_2CF=CFCF_3$ | 1,1,1,2,3,4,4-heptafluoro-2-butene |
| HFC-1327et | $(CF_3)_2C=CHF$ | 1,3,3,3-tetrafluoro-2-(trifluoromethyl)-1-propene |
| HFC-1327cz | $CF_2=CHCF_2CF_3$ | 1,1,3,3,4,4,4-heptafluoro-1-butene |
| HFC-1327cye | $CF_2=CFCHFCF_3$ | 1,1,2,3,4,4,4-heptafluoro-1-butene |
| HFC-1327cyc | $CF_2=CFCF_2CHF_2$ | 1,1,2,3,3,4,4-heptafluoro-1-butene |
| HFC-1336yf | $CF_3CF_2CF=CH_2$ | 2,3,3,4,4,4-hexafluoro-1-butene |
| HFC-1336mzz | $CF_3CH=CHCF_3$ | 1,1,1,4,4,4-hexafluoro-2-butene |
| HFC-1336ze | $CHF=CHCF_2CF_3$ | 1,3,3,4,4,4-hexafluoro-1-butene |
| HFC-1336eye | $CHF=CFCHFCF_3$ | 1,2,3,4,4,4-hexafluoro-1-butene |
| HFC-1336eyc | $CHF=CFCF_2CHF_2$ | 1,2,3,3,4,4-hexafluoro-1-butene |
| HFC-1336pyy | $CHF_2CF=CFCHF_2$ | 1,1,2,3,4,4-hexafluoro-2-butene |
| HFC-1336qy | $CH_2FCF=CFCF_3$ | 1,1,1,2,3,4-hexafluoro-2-butene |
| HFC-1336pz | $CHF_2CH=CFCF_3$ | 1,1,1,2,4,4-hexafluoro-2-butene |
| HFC-1336mzy | $CF_3CH=CFCHF_2$ | 1,1,1,3,4,4-hexafluoro-2-butene |
| HFC-1336qc | $CF_2=CFCF_2CH_2F$ | 1,1,2,3,3,4-hexafluoro-1-butene |
| HFC-1336pe | $CF_2=CFCHFCHF_2$ | 1,1,2,3,4,4-hexafluoro-1-butene |
| HFC-1336ft | $CH_2=C(CF_3)_2$ | 3,3,3-trifluoro-2-(trifluoromethyl)-1-propene |
| HFC-1345qz | $CH_2FCH=CFCF_3$ | 1,1,1,2,4-pentafluoro-2-butene |
| HFC-1345mzy | $CF_3CH=CFCH_2F$ | 1,1,1,3,4-pentafluoro-2-butene |
| HFC-1345fz | $CF_3CF_2CH=CH_2$ | 3,3,4,4,4-pentafluoro-1-butene |
| HFC-1345mzz | $CHF_2CH=CHCF_3$ | 1,1,1,4,4-pentafluoro-2-butene |
| HFC-1345sy | $CH_3CF=CFCF_3$ | 1,1,1,2,3-pentafluoro-2-butene |
| HFC-1345fyc | $CH_2=CFCF_2CHF_2$ | 2,3,3,4,4-pentafluoro-1-butene |
| HFC-1345pyz | $CHF_2CF=CHCHF_2$ | 1,1,2,4,4-pentafluoro-2-butene |
| HFC-1345cyc | $CH_3CF_2CF=CF_2$ | 1,1,2,3,3-pentafluoro-1-butene |
| HFC-1345pyy | $CHF_2CF=CFCHF_2$ | 1,1,2,3,4-pentafluoro-2-butene |
| HFC-1345eyc | $CH_2FCF_2CF=CF_2$ | 1,2,3,3,4-pentafluoro-1-butene |
| HFC-1345ctm | $CF_2=C(CF_3)(CH_3)$ | 1,1,3,3,3-pentafluoro-2-methyl-1-propene |
| HFC-1345ftp | $CH_2=C(CHF_2)(CF_3)$ | 2-(difluoromethyl)-3,3,3-trifluoro-1-propene |
| HFC-1354fzc | $CH_2=CHCF_2CHF_2$ | 3,3,4,4-tetrafluoro-1-butene |
| HFC-1354ctp | $CF_2=C(CHF_2)(CH_3)$ | 1,1,3,3-tetrafluoro-2-methyl-1-propene |
| HFC-1354etm | $CHF=C(CF_3)(CH_3)$ | 1,3,3,3-tetrafluoro-2-methyl-1-propene |
| HFC-1354tfp | $CH_2=C(CHF_2)_2$ | 2-(difluoromethyl)-3,3-difluoro-1-propene |
| HFC-1354my | $CF_3CF=CFCH_3$ | 1,1,1,2-tetrafluoro-2-butene |
| HFC-1354mzy | $CH_3CF=CHCF_3$ | 1,1,1,3-tetrafluoro-2-butene |
| FC-141-10myy | $CF_3CF=CFCF_2CF_3$ | 1,1,1,2,3,4,4,5,5,5-decafluoro-2-pentene |
| FC-141-10cy | $CF_2=CFCF_2CF_2CF_3$ | 1,1,2,3,3,4,4,5,5,5-decafluoro-1-pentene |
| HFC-1429mzt | $(CF_3)_2C=CHCF_3$ | 1,1,1,4,4,4-hexafluoro-2-(trifluoromethyl)-2-butene |
| HFC-1429myz | $CF_3CF=CHCF_2CF_3$ | 1,1,1,2,4,4,5,5,5-nonafluoro-2-pentene |
| HFC-1429mzy | $CF_3CH=CFCF_2CF_3$ | 1,1,1,3,4,4,5,5,5-nonafluoro-2-pentene |
| HFC-1429eyc | $CHF=CFCF_2CF_2CF_3$ | 1,2,3,3,4,4,5,5,5-nonafluoro-1-pentene |
| HFC-1429czc | $CF_2=CHCF_2CF_2CF_3$ | 1,1,3,3,4,4,5,5,5-nonafluoro-1-pentene |
| HFC-1429cycc | $CF_2=CFCF_2CF_2CHF_2$ | 1,1,2,3,3,4,4,5,5-nonafluoro-1-pentene |
| HFC-1429pyy | $CHF_2CF=CFCF_2CF_3$ | 1,1,2,3,4,5,5,5-nonafluoro-2-pentene |
| HFC-1429myyc | $CF_3CF=CFCF_2CHF_2$ | 1,1,1,2,3,4,4,5,5-nonafluoro-2-pentene |
| HFC-1429myye | $CF_3CF=CFCHFCF_3$ | 1,1,1,2,3,4,5,5,5-nonafluoro-2-pentene |
| HFC-1429eyym | $CHF=CFCF(CF_3)_2$ | 1,2,3,4,4,4-hexafluoro-3-(trifluoromethyl)-butene |
| HFC-1429cyzm | $CF_2=CFCH(CF_3)_2$ | 1,1,2,4,4,4-hexafluoro-3-(trifluoromethyl)-1-butene |
| HFC-1429mzt | $CF_3CH=C(CF_3)_2$ | 1,1,1,4,4,4-hexafluoro-3-(trifluoromethyl)-2-butene |
| HFC-1429czym | $CF_2=CHCF(CF_3)_2$ | 1,1,3,4,4,4-hexafluoro-3-(trifluoromethyl)-1-butene |
| HFC-1438fy | $CH_2=CFCF_2CF_2CF_3$ | 2,3,3,4,4,5,5,5-octafluoro-1-pentene |
| HFC-1438eycc | $CHF=CFCF_2CF_2CHF_2$ | 1,2,3,3,4,4,5,5-octafluoro-1-pentene |
| HFC-1438ftmc | $CH_2=C(CF_3)CF_2CF_3$ | 3,3,4,4,4-pentafluoro-2-(trifluoromethyl)-1-butene |
| HFC-1438czzm | $CF_2=CHCH(CF_3)_2$ | 1,1,4,4,4-pentafluoro-3-(trifluoromethyl)-1-butene |
| HFC-1438ezym | $CHF=CHCF(CF_3)_2$ | 1,3,4,4,4-pentafluoro-3-(trifluoromethyl)-1-butene |

TABLE 2-continued

| Code | Structure | Chemical name |
|---|---|---|
| HFC-1438ctmf | $CF_2=C(CF_3)CH_2CF_3$ | 1,1,4,4,4-pentafluoro-2-(trifluoromethyl)-1-butene |
| HFC-1438mzz | $CF_3CH=CHCF_2CF_3$ | 1,1,1,4,4,5,5,5-octafluoro-2-pentene |
| HFC-1447fzy | $(CF_3)_2CFCH=CH_2$ | 3,4,4,4-tetrafluoro-3-(trifluoromethyl)-1-butene |
| HFC-1447fz | $CF_3CF_2CF_2CH=CH_2$ | 3,3,4,4,5,5,5-heptafluoro-1-pentene |
| HFC-1447fycc | $CH_2=CFCF_2CF_2CHF_2$ | 2,3,3,4,4,5,5-heptafluoro-1-pentene |
| HFC-1447czcf | $CF_2=CHCF_2CH_2CF_3$ | 1,1,3,3,5,5,5-heptafluoro-1-pentene |
| HFC-1447mytm | $CF_3CF=C(CF_3)(CH_3)$ | 1,1,1,2,4,4,4-heptafluoro-3-methyl-2-butene |
| HFC-1447fyz | $CH_2=CFCH(CF_3)_2$ | 2,4,4,4-tetrafluoro-3-(trifluoromethyl)-1-butene |
| HFC-1447ezz | $CHF=CHCH(CF_3)_2$ | 1,4,4,4-tetrafluoro-3-(trifluoromethyl)-1-butene |
| HFC-1447qzt | $CH_2FCH=C(CF_3)_2$ | 1,4,4,4-tetrafluoro-3-(trifluoromethyl)-2-butene |
| HFC-1447syt | $CH_3CF=C(CF_3)_2$ | 2,4,4,4-tetrafluoro-3-(trifluoromethyl)-2-butene |
| HFC-1456szt | $(CF_3)_2C=CHCH_3$ | 3-(trifluoromethyl)-4,4,4-trifluoro-2-butene |
| HFC-1456szy | $CF_3CF_2CF=CHCH_3$ | 3,4,4,5,5,5-hexafluoro-2-pentene |
| HFC-1456mstz | $CF_3C(CH_3)=CHCF_3$ | 1,1,1,4,4,4-hexafluoro-2-methyl-2-butene |
| HFC-1456fzce | $CH_2=CHCF_2CHFCF_3$ | 3,3,4,5,5,5-hexafluoro-1-pentene |
| HFC-1456ftmf | $CH_2=C(CF_3)CH_2CF_3$ | 4,4,4-trifluoro-2-(trifluoromethyl)-1-butene |
| FC-151-12c | $CF_3(CF_2)_3CF=CF_2$ | 1,1,2,3,3,4,4,5,5,6,6,6-dodecafluoro-1-hexene (or perfluoro-1-hexene) |
| FC-151-12mcy | $CF_3CF_2CF=CFCF_2CF_3$ | 1,1,1,2,2,3,4,5,5,6,6,6-dodecafluoro-3-hexene (or perfluoro-3-hexene) |
| FC-151-12mmtt | $(CF_3)_2C=C(CF_3)_2$ | 1,1,1,4,4,4-hexafluoro-2,3-bis(trifluoromethyl)-2-butene |
| FC-151-12mmzz | $(CF_3)_2CFCF=CFCF_3$ | 1,1,1,2,3,4,5,5,5-nonafluoro-4-(trifluoromethyl)-2-pentene |
| HFC-152-11mmtz | $(CF_3)_2C=CHC_2F_5$ | 1,1,1,4,4,5,5,5-octafluoro-2-(trifluoromethyl)-2-pentene |
| HFC-152-11mmyyz | $(CF_3)_2CFCF=CHCF_3$ | 1,1,1,3,4,5,5,5-octafluoro-4-(trifluoromethyl)-2-pentene |
| HFC-153-10mmyzz | $CF_3CH=CHCF(CF_3)_2$ | 1,1,1,4,5,5,5-heptafluoro-4-(trifluoromethyl)-2-pentene |
| HFC-153-10mzz | $CF_3CH=CHCF_2CF_2CF_3$ | 1,1,1,4,4,5,5,6,6,6-decafluoro-2-hexene |
| HFC-153-10mczz | $CF_3CF_2CH=CHCF_2CF_3$ | 1,1,1,2,2,5,5,6,6,6-decafluoro-3-hexene |
| PFBE (or HFC-1549fz) | $CF_3CF_2CF_2CF_2CH=CH_2$ | 3,3,4,4,5,5,6,6,6-nonafluoro-1-hexene (or perfluorobutylethylene) |
| HFC-1549fztmm | $CH_2=CHC(CF_3)_3$ | 4,4,4-trifluoro-3,3-bis(trifluoromethyl)-1-butene |
| HFC-1549mmtts | $(CF_3)_2C=C(CH_3)(CF_3)$ | 1,1,1,4,4,4-hexafluoro-3-methyl-2-(trifluoromethyl)-2-butene |
| HFC-1549fycz | $CH_2=CFCF_2CH(CF_3)_2$ | 2,3,3,5,5,5-hexafluoro-4-(trifluoromethyl)-1-pentene |
| HFC-1549myts | $CF_3CF=C(CH_3)CF_2CF_3$ | 1,1,1,2,4,4,5,5,5-nonafluoro-3-methyl2-pentene |
| HFC-1549mzzz | $CF_3CH=CHCH(CF_3)_2$ | 1,1,1,5,5,5-hexafluoro-4-(trifluoromethyl)-2-pentene |
| HFC-1558szy | $CF_3CF_2CF_2CF=CHCH_3$ | 3,4,4,5,5,6,6,6-octafluoro-2-hexene |
| HFC-1558fzccc | $CH_2=CHCF_2CF_2CF_2CHF_2$ | 3,3,4,4,5,5,6,6-octafluoro-2-hexene |
| HFC-1558mmtzc | $(CF_3)_2C=CHCF_2CH_3$ | 1,1,1,4,4-pentafluoro-2-(trifluoromethyl)-2-pentene |
| HFC-1558ftmf | $CH_2=C(CF_3)CH_2C_2F_5$ | 4,4,5,5,5-pentafluoro-2-(trifluoromethyl)-1-pentene |
| HFC-1567fts | $CF_3CF_2CF_2C(CH_3)=CH_2$ | 3,3,4,4,5,5,5-heptafluoro-2-methyl-1-pentene |
| HFC-1567szz | $CF_3CF_2CF_2CH=CHCH_3$ | 4,4,5,5,6,6,6-heptafluoro-2-hexene |
| HFC-1567fzfc | $CH_2=CHCH_2CF_2C_2F_5$ | 4,4,5,5,6,6,6-heptafluoro-1-hexene |
| HFC-1567sfyy | $CF_3CF_2CF=CFC_2H_5$ | 1,1,1,2,2,3,4-heptafluoro-3-hexene |
| HFC-1567fzfy | $CH_2=CHCH_2CF(CF_3)_2$ | 4,5,5,5-tetrafluoro-4-(trifluoromethyl)-1-pentene |
| HFC-1567myzzm | $CF_3CF=CHCH(CF_3)(CH_3)$ | 1,1,1,2,5,5,5-heptafluoro-4-methyl-2-pentene |
| HFC-1567mmtyf | $(CF_3)_2C=CFC_2H_5$ | 1,1,1,3-tetrafluoro-2-(trifluoromethyl)-2-pentene |
| FC-161-14myy | $CF_3CF=CFCF_2CF_2C_2F_5$ | 1,1,1,2,3,4,4,5,5,6,6,7,7,7-tetradecafluoro-2-heptene |
| FC-161-14mcyy | $CF_3CF_2CF=CFCF_2C_2F_5$ | 1,1,1,2,2,3,4,5,5,6,6,7,7,7-tetradecafluoro-2-heptene |
| HFC-162-13mzy | $CF_3CH=CFCF_2CF_2C_2F_5$ | 1,1,1,3,4,4,5,5,6,6,7,7,7-tridecafluoro-2-heptene |

TABLE 2-continued

| Code | Structure | Chemical name |
|---|---|---|
| HFC162-13myz | $CF_3CF{=}CHCF_2CF_2C_2F_5$ | 1,1,1,2,4,4,5,5,6,6,7,7,7-tridecafluoro-2-heptene |
| HFC-162-13mczy | $CF_3CF_2CH{=}CFCF_2C_2F_5$ | 1,1,1,2,2,4,5,5,6,6,7,7,7-tridecafluoro-3-heptene |
| HFC-162-13mcyz | $CF_3CF_2CF{=}CHCF_2C_2F_5$ | 1,1,1,2,2,3,5,5,6,6,7,7,7-tridecafluoro-3-heptene |
| HFC-C1316cc | cyclo-$CF_2CF_2CF{=}CF{-}$ | 1,2,3,3,4,4-hexafluorocyclobutene |
| HFC-C1334cc | cyclo-$CF_2CF_2CH{=}CH{-}$ | 3,3,4,4-tetrafluorocyclobutene |
| HFC-C1436 | cyclo-$CF_2CF_2CF_2CH{=}CH{-}$ | 3,3,4,4,5,5,-hexafluorocyclopentene |
| HFC-C1418y | cyclo-$CF_2CF{=}CFCF_2CF_2{-}$ | 1,2,3,3,4,4,5,5-octafluorocyclopentene |
| FC-C151-10y | cyclo-$CF_2CF{=}CFCF_2CF_2CF_2{-}$ | 1,2,3,3,4,4,5,5,6,6-decafluorocyclohexene |

The compounds listed in Table 2 are available commercially or may be prepared by processes known in the art or as described herein.

1,1,1,4,4-pentafluoro-2-butene may be prepared from 1,1,1,2,4,4-hexafluorobutane ($CHF_2CH_2CHFCF_3$) by dehydrofluorination over solid KOH in the vapor phase at room temperature. The synthesis of 1,1,1,2,4,4-hexafluorobutane is described in U.S. Pat. No. 6,066,768, incorporated herein by reference.

1,1,1,4,4,4-hexafluoro-2-butene may be prepared from 1,1,1,4,4,4-hexafluoro-2-iodobutane ($CF_3CHICH_2CF_3$) by reaction with KOH using a phase transfer catalyst at about 60° C. The synthesis of 1,1,1,4,4,4-hexafluoro-2-iodobutane may be carried out by reaction of perfluoromethyl iodide ($CF_3I$) and 3,3,3-trifluoropropene ($CF_3CH{-}CH_2$) at about 200° C. under autogenous pressure for about 8 hours.

3,4,4,5,5,5-hexafluoro-2-pentene may be prepared by dehydrofluorination of 1,1,1,2,2,3,3-heptafluoropentane ($CF_3CF_2CF_2CH_2CH_3$) using solid KOH or over a carbon catalyst at 200-300° C. 1,1,1,2,2,3,3-heptafluoropentane may be prepared by hydrogenation of 3,3,4,4,5,5,5-heptafluoro-1-pentene ($CF_3CF_2CF_2CH{=}CH_2$).

1,1,1,2,3,4-hexafluoro-2-butene may be prepared by dehydrofluorination of 1,1,1,2,3,3,4-heptafluorobutane ($CH_2FCF_2CHFCF_3$) using solid KOH.

1,1,1,2,4,4-hexafluoro-2-butene may be prepared by dehydrofluorination of 1,1,1,2,2,4,4-heptafluorobutane ($CHF_2CH_2CF_2CF_3$) using solid KOH.

1,1,1,3,4,4-hexafluoro2-butene may be prepared by dehydrofluorination of 1,1,1,3,3,4,4-heptafluorobutane ($CF_3CH_2CF_2CHF_2$) using solid KOH.

1,1,1,2,4-pentafluoro-2-butene may be prepared by dehydrofluorination of 1,1,1,2,2,3-hexafluorobutane ($CH_2FCH_2CF_2CF_3$) using solid KOH.

1,1,1,3,4-pentafluoro-2-butene may be prepared by dehydrofluorination of 1,1,1,3,3,4-hexafluorobutane ($CF_3CH_2CF_2CH_2F$) using solid KOH.

1,1,1,3-tetrafluoro-2-butene may be prepared by reacting 1,1,1,3,3-pentafluorobutane ($CF_3CH_2CF_2CH_3$) with aqueous KOH at 120° C.

1,1,1,4,4,5,5,5-octafluoro-2-pentene may be prepared from ($CF_3CHICH_2CF_2CF_3$) by reaction with KOH using a phase transfer catalyst at about 60° C. The synthesis of 4-iodo-1,1,1,2,2,5,5,5-octafluoropentane may be carried out by reaction of perfluoroethyliodide ($CF_3CF_2I$) and 3,3,3-trifluoropropene at about 200° C. under autogenous pressure for about 8 hours.

1,1,1,2,2,5,5,6,6,6-decafluoro-3-hexene may be prepared from 1,1,1,2,2,5,5,6,6,6-decafluoro-3-iodohexane ($CF_3CF_2CHICH_2CF_2CF_3$) by reaction with KOH using a phase transfer catalyst at about 60° C. The synthesis of 1,1,1,2,2,5,5,6,6,6-decafluoro-3-iodohexane may be carried out by reaction of perfluoroethyliodide ($CF_3CF_2I$) and 3,3,4,4,4-pentafluoro-1-butene ($CF_3CF_2CH{=}CH_2$) at about 200° C. under autogenous pressure for about 8 hours.

1,1,1,4,5,5,5-heptafluoro-4-(trifluoromethyl)-2-pentene may be prepared by the dehydrofluorination of 1,1,1,2,5,5,5-heptafluoro-4-iodo-2-(trifluoromethyl)-pentane ($CF_3CHICH_2CF(CF_3)_2$) with KOH in isopropanol. $CF_3CHICH_2CF(CF_3)_2$ is made from reaction of $(CF_3)_2CFI$ with $CF_3CH{=}CH_2$ at high temperature, such as about 200° C.

1,1,1,4,4,5,5,6,6,6-decafluoro-2-hexene may be prepared by the reaction of 1,1,1,4,4,4-hexafluoro-2-butene ($CF_3CH{=}CHCF_3$) with tetrafluoroethylene ($CF_2{=}CF_2$) and antimony pentafluoride ($SbF_5$).

2,3,3,4,4-pentafluoro-1-butene may be prepared by dehydrofluorination of 1,1,2,2,3,3-hexafluorobutane over fluorided alumina at elevated temperature.

2,3,3,4,4,5,5,5-ocatafluoro-1-pentene may be prepared by dehydrofluorination of 2,2,3,3,4,4,5,5,5-nonafluoropentane over solid KOH.

1,2,3,3,4,4,5,5-octafluoro-1-pentene may be prepared by dehydrofluorination of 2,2,3,3,4,4,5,5,5-nonafluoropentane over fluorided alumina at elevated temperature.

In one embodiment, the present composition comprising a fluoroolefin may further comprises at least one compound selected from the group consisting of: HFC-1225ye, HFC-1234ze, HFC-1234yf, HFC-1234ye, HFC-1243zf, HFC-32, HFC-125, HFC-134, HFC-134a, HFC-143a, HFC-152a, HFC-161, HFC-227ea, HFC-236ea, HFC-236fa, HFC-245fa, HFC-365mfc, propane, n-butane, isobutane, 2-methylbutane, n-pentane, cyclopentane, dimethylether, $CF_3SCF_2$, $CO_2$, ammonia, and $CF_3I$.

Many of the compounds of Formula I, Table 1 and Table 2 exist as different configurational isomers or stereoisomers. When the specific isomer is not designated, the present invention is intended to include all single configurational isomers, single stereoisomers, or any combination thereof. For instance, F11E is meant to represent the E-isomer, Z-isomer, or any combination or mixture of both isomers in any ratio. As another example, HFC-1225ye is meant to represent the E-isomer, Z-isomer, or any combination or mixture of both isomers in any ratio.

The heat transfer fluid compositions of the present invention may be generally useful when the fluoroolefin is present at about 1 weight percent to about 99 weight percent, preferably about 20 weight percent to about 99 weight percent, more preferably about 40 weight percent to about 99 weight percent and still more preferably 50 weight percent to about 99 weight percent.

The present invention further provides compositions as listed in Table 3.

TABLE 3

| Components | Concentration ranges (wt %) | | |
|---|---|---|---|
| | Preferred | More preferred | Most preferred |
| HFC-1225ye/HFC-32 | 1-99/99-1 | 30-99/70-1 | 90-99/10-1; 95/5/97/3 |
| HFC-1225ye/HFC-134a | 1-99/99-1 | 40-99/60-1 | 90/10 |
| HFC-1225ye/CO$_2$ | 0.1-99.9/99.9-0.1 | 70-99.7/30-0.3 | 99/1 |
| HFC-1225ye/ammonia | 0.1-99.9/0.1-99.9 | 40-99.9/0.1-60 | 90/10, 85/15, 80/20, 95/5 |
| HFC-1225ye/HFC-1234yf | 1-99/99-1 | 51-99/49-1 and 60-90/40-10 | 60/40, 51/49 |
| HFC-1225ye/HFC-152a/HFC-32 | 1-98/1-98/1-98 | 50-98/1-40/1-40 | 85/10/5 81/15/4 82/15/3 |
| HFC-1225ye/HFC-152a/CO$_2$ | 1-98/1-98/0.1-98 | 50-98/1-40/0.3-30 | 84/15/1 84/15.5/0.5 |
| HFC-1225ye/HFC-152a/propane | 1-98/1-98/1-98 | 50-98/1-40/1-20 | 85/13/2 |
| HFC-1225ye/HFC-152a/i-butane | 1-98/1-98/1-98 | 50-98/1-40/1-20 | 85/13/2 |
| HFC-1225ye/HFC-152a/DME | 1-98/1-98/1-98 | 50-98/1-40/1-20 | 85/13/2 |
| HFC-1225ye/HFC-152a/CF$_3$I | 1-98/1-98/1-98 | 20-90/1-50/1-60 | |
| HFC-1225ye/HFC-134a/HFC-152a | 1-98/1-98/1-98 | 40-98/1-50/1-40 | 76/9/15 |
| HFC-1225ye/HFC-134a/HFC-32 | 1-98/1-98/1-98 | 1-80/1-80/1-80 | 88/9/3 |
| HFC-1225ye/HFC-134a/HFC-161 | 1-98/1-98/1-98 | 40-98/1-50/1-20 | 86/10/4 |
| HFC-1225ye/HFC-134a/CO$_2$ | 1-98/1-98/0.1-98 | 40-98/1-50/0.3-30 | 88.5/11/0.5 |
| HFC-1225ye/HFC-134a/propane | 1-98/1-98/1-98 | 40-98/1-50/1-20 | 87/10/3 |
| HFC-1225ye/HFC-134a/i-butane | 1-98/1-98/1-98 | 40-98/1-50/1-20 | 87/10/3 |
| HFC-1225ye/HFC-134a/DME | 1-98/1-98/1-98 | 40-98/1-50/1-20 | 87/10/3 |
| HFC-1225ye/HFC-134/HFC-32 | 1-98/1-98/1-98 | 40-98/1-50/1-40 | 88/9/3 |
| trans-HFC-1234ze/HFC-134a | 1-99/99-1 | 30-99/70-1 | 90/10 |
| trans-HFC-1234ze/HFC-32 | 1-99/99-1 | 40-99/60-1 | 95/5 |
| trans-HFC-1234ze/HFC-32/CF$_3$I | 1-98/1-98/1-98 | 20-90/0.1-60/1-70 | |
| trans-HFC-1234ze/HFC-152a | 1-99/99-1 | 40-99/60-1 | 80/20 |
| trans-HFC-1234ze/HFC-125 | 1-99/99-1 | 30-99/70-1 | |
| HFC-1234yf/HFC-134a | 1-99/99-1 | 30-99/70-1 | 90/10 |
| HFC-1234yf/HFC-32 | 1-99/99-1 | 40-99/60-1 | 95/5 |
| HFC-1234yf/HFC-125 | 0.1-99/99-0.1 | 52-99/48-1 | |
| HFC-1234yf/HFC-152a | 1-99/99-1 | 40-99/60-1 | 80/20 |
| HFC-1225ye/HFC-134a/HFC-152a/HFC-32 | 1-97/1-97/1-97/0.1-97 | 20-97/1-80/1-50/0.1-50 | 74/8/17/1 |
| HFC-1225ye/HFC-1234yf/HFC-134a | 1-98/1-98/0.1-98 | 10-90/10-90/0.1-50 | 70/20/10 and 20/70/10 |
| HFC-1225ye/HFC-1234yf/HFC-32 | 1-98/1-98/0.1-98 | 10-90/5-90/0.1-50 | 25/73/2, 75/23/2, 49/49/2, 85/10/5, 90/5/5 |
| HFC-1225ye/HFC-1234yf/HFC-32/CF$_3$I | 1-97/1-97/0.1-97/1-97 | 10-80/10-80/1-60/1-60 | |
| HFC-1225ye/HFC-1234yf/HFC-152a | 1-98/1-98/0.1-98 | 10-90/10-90/0.1-50 | 70/25/5 and 25/70/5 |
| HFC-1225ye/HFC-1234yf/HFC-125 | 1-98/1-98/0.1-98 | 10-90/10-90/0.1-50 | 25/71/4, 75/21/4, 75/24/1 and 25/74/1 |
| HFC-1225ye/HFC-1234yf/CF$_3$I | 1-98/1-98/1-98 | 9-90/9-90/1-60 | 40/40/20 and 45/45/10 |
| HFC-32/HFC-125/HFC-1225ye | 0.1-98/0.1-98/0.1-98 | 5-70/5-70/5-70 | 30/30/40 and 23/25/52 |
| HFC-32/HFC-125/trans-HFC-1234ze | 0.1-98/0.1-98/0.1-98 | 5-70/5-70/5-70 | 30/50/20 and 23/25/52 |
| HFC-32/HFC-125/HFC-1234yf | 0.1-98/0.1-98/0.1-98 | 5-70/5-70/5-70 | 40/50/10, 23/25/52, 15/45/40, and 10/60/30 |
| HFC-32/HFC-134a/HFC-1225ye/CF$_3$I | 1-97/1-97/1-97/1-97 | 1-60/1-60/1-60/1-60 | |
| HFC-32/HFC-134a/HFC-1225ye/HFC-1234yf/CF$_3$I | 1-96/1-96/1-96/1-96/1-96 | 1-50/1-50/1-50/1-50/1-50 | |
| HFC-32/HFC-125/HFC-134a/HFC-1225ye/CF$_3$I | 1-96/1-96/1-96/1-96/1-96 | 1-50/1-50/1-50/1-50/1-50 | |
| HFC-125/HFC-1225ye/n-butane | 0.1-98/0.1-98/0.1-98 | 5-70/5-70/1-20 | 65/32/3 and 85.1/11.5/3.4 |
| HFC-32/NH$_3$/HFC-1225ye | 1-98/1-98/1-98 | 1-60/10-60/10-90 | |
| HFC-32/NH$_3$/HFC-1225ye/CF$_3$I | 1-97/1-97/1-97/1-97 | 1-60/1-60/10-80/1-60 | |
| HFC-32/NH$_3$/HFC-1234yf/CF$_3$I | 1-97/1-97/1-97/1-97 | 1-60/1-60/10-80/5-80 | |
| HFC-125/trans-HFC-1234ze/n-butane | 0.1-98/0.1-98/0.1-98 | 5-70/5-70/1-20 | 66/32/2 and 86.1/11.5/2.4 |

TABLE 3-continued

| Components | Concentration ranges (wt %) | | |
|---|---|---|---|
| | Preferred | More preferred | Most preferred |
| HFC-125/HFC-1234yf/n-butane | 0.1-98/0.1-98/0.1-98 | 5-70/5-70/1-20 | 67/32/1 and 87.1/11.5/1.4 |
| HFC-125/HFC-1225ye/isobutane | 0.1-98/0.1-98/0.1-98 | 5-70/5-70/1-20 | 85.1/11.5/3.4 and 65/32/3 |
| HFC-1225ye/HFC-125/ammonia | 0.1-98/0.1-98/0.1-98 | 20-98/1-60/0.1-40 | |
| HFC-1225ye/HFC-32/HFC-125/ammonia | 0.1-97/0.1-97/0.1-97/0.1-97 | 20-97/1-60/1-60/0.1-40 | |
| HFC-125/trans-HFC-1234ze/isobutane | 0.1-98/0.1-98/0.1-98 | 5-70/5-70/1-20 | 86.1/11.5/2.4 and 66/32/2 |
| HFC-125/HFC-1234yf/isobutane | 0.1-98/0.1-98/0.1-98 | 5-70/5-70/1-20 and 80-98/1-19/1-10 | 87.1/11.5/1.4 and 67/32/1 |
| HFC-1234yf/HFC-32/HFC-143a | 1-50/1-98/1-98 | 15-50/20-80/5-60 | |
| HFC-1234yf/HFC-32/isobutane | 1-40/59-98/1-30 | 10-40/59-90/1-10 | |
| HFC-1234yf/HFC-125/HFC-143a | 1-60/1-98/1-98 | 10-60/20-70/20-70 | |
| HFC-1234yf/HFC-125/isobutane | 1-40/59-98/1-20 | 10-40/59-90/1-10 | |
| HFC-1234yf/HFC-125/$CF_3I$ | 1-98/0.1-98/1-98 | 10-80/1-60/1-60 | |
| HFC-1234yf/HFC-134/propane | 1-80/1-70/19-90 | 20-80/10-70/19-50 | |
| HFC-1234yf/HFC-134/DME | 1-70/1-98/29-98 | 20-70/10-70/29-50 | |
| HFC-1234yf/HFC-134a/propane | 1-80/1-80/19-98 | 10-80/10-80/19-50 | |
| HFC-1234yf/HFC-134a/n-butane | 1-98/1-98/1-30 | 10-80/10-80/1-20 | |
| HFC-1234yf/HFC-134a/isobutane | 1-98/1-98/1-30 | 10-80/10-80/1-20 | |
| HFC-1234yf/HFC-134a/DME | 1-98/1-98/1-40 | 10-80/10-80/1-20 | |
| HFC-1234yf/HFC-134a/$CF_3I$ | 1-98/1-98/1-98 | 10-80/1-60/1-60 | |
| HFC-1234yf/HFC-143a/propane | 1-80/1-98/1-98 | 10-80/10-80/1-50 | |
| HFC-1234yf/HFC-143a/DME | 1-40/59-98/1-20 | 5-40/59-90/1-10 | |
| HFC-1234yf/HFC-152a/n-butane | 1-98/1-98/1-30 | 10-80/10-80/1-20 | |
| HFC-1234yf/HFC-152a/isobutane | 1-98/1-90/1-40 | 10-80/10-80/1-20 | |
| HFC-1234yf/HFC-152a/DME | 1-70/1-98/1-98 | 10-70/10-80/1-20 | |
| HFC-1234yf/HFC-152a/$CF_3I$ | 1-98/1-98/1-98 | 10-80/1-60/1-60 | |
| HFC-1234yf/HFC-227ea/propane | 1-80/1-70/29-98 | 10-60/10-60/29-50 | |
| HFC-1234yf/HFC-227ea/n-butane | 40-98/1-59/1-20 | 50-98/10-49/1-10 | |
| HFC-1234yf/HFC-227ea/isobutane | 30-98/1-69/1-30 | 50-98/10-49/1-10 | |
| HFC-1234yf/HFC-227ea/DME | 1-98/1-80/1-98 | 10-80/10-80/1-20 | |
| HFC-1234yf/n-butane/DME | 1-98/1-40/1-98 | 10-80/1-40/1-20 | |
| HFC-1234yf/isobutane/DME | 1-98/1-50/1-98 | 10-90/1-40/1-20 | |
| HFC-1234yf/DME/$CF_3I$ | 1-98/1-98/1-98 | 10-80/1-20/10-80 | |
| HFC-1234yf/DME/$CF_3SCF_3$ | 1-98/1-40/1-98 | 10-80/1-20/10-70 | |
| HFC-1225ye/trans-HFC-1234ze/HFC-134 | 1-98/1-98/1-98 | 10-80/10-80/10-80 | |
| HFC-1225ye/trans-HFC-1234ze/HFC-227ea | 1-98/1-98/1-98 | 10-80/10-80/10-80 | |
| HFC-1225ye/trans-HFC-1234ze/propane | 1-60/1-60/39-98 | 10-60/10-60/39-80 | |
| HFC-1225ye/trans-HFC-1234ze/n-butane | 1-98/1-98/1-30 | 10-80/10-80/1-20 | |
| HFC-1225ye/trans-HFC-1234ze/DME | 1-98/1-98/1-98 | 10-80/10-80/1-30 | |
| HFC-1225ye/trans-HFC-1234ze/$CF_3SCF_3$ | 1-98/1-98/1-98 | 10-80/10-80/10-80 | |
| HFC-1225ye/HFC-1243zf/HFC-134 | 1-98/1-98/1-98 | 10-80/10-80/10-80 | |
| HFC-1225ye/HFC-1243zf/n-butane | 1-98/1-98/1-30 | 10-80/10-80/1-20 | |
| HFC-1225ye/HFC-1243zf/isobutane | 1-98/1-98/1-40 | 10-80/10-80/1-30 | |
| HFC-1225ye/HFC-1243zf/DME | 1-98/1-98/1-98 | 10-80/10-80/1-30 | |
| HFC-1225ye/HFC-1243zf/$CF_3I$ | 1-98/1-98/1-98 | 10-80/10-80/10-80 | |
| HFC-1225ye/HFC-134/HFC-152a | 1-98/1-98/1-98 | 10-80/10-80/1-50 | |
| HFC-1225ye/HFC-134/HFC-227ea | 1-98/1-98/1-98 | 10-80/10-80/10-80 | |
| HFC-1225ye/HFC-134/n-butane | 1-98/1-90/1-40 | 10-80/10-80/1-30 | |
| HFC-1225ye/HFC-134/isobutane | 1-98/1-90/1-40 | 10-80/10-80/1-30 | |
| HFC-1225ye/HFC-134/DME | 1-98/1-98/1-40 | 10-80/10-80/1-30 | |
| HFC-1225ye/HFC-227ea/DME | 40-98/1-59/1-30 | 50-98/1-49/1-20 | |
| HFC-1225ye/n-butane/DME | 1-98/1-30/1-98 | 60-98/1-20/1-20 | |
| HFC-1225ye/n-butane/$CF_3SCF_3$ | 1-98/1-20/1-98 | 10-80/1-10/10-80 | |
| HFC-1225ye/isobutane/DME | 1-98/1-60/1-98 | 40-90/1-30/1-30 | |
| HFC-1225ye/isobutane/$CF_3I$ | 1-98/1-40/1-98 | 10-80/1-30/10-80 | |
| trans-HFC-1234ze/HFC-1243zf/HFC-227ea | 1-98/1-98/1-98 | 10-80/10-80/10-80 | |
| trans-HFC-1234ze/HFC-1243zf/n-butane | 1-98/1-98/1-30 | 10-80/10-80/1-20 | |
| trans-HFC-1234ze/HFC-1243zf/isobutane | 1-98/1-98/1-40 | 10-80/10-80/1-30 | |

TABLE 3-continued

| Components | Concentration ranges (wt %) | | |
|---|---|---|---|
| | Preferred | More preferred | Most preferred |
| trans-HFC-1234ze/HFC-1243zf/DME | 1-98/1-98/1-98 | 10-80/10-80/1-40 | |
| trans-HFC-1234ze/HFC-32/CF3I | 1-98/1-98/1-98 | 10-80/1-70/1-80 | |
| trans-HFC-1234ze/HFC-134/HFC-152a | 1-98/1-98/1-98 | 10-80/10-80/1-50 | |
| trans-HFC-1234ze/HFC-134/HFC-227ea | 1-98/1-98/1-98 | 10-80/10-80/10-80 | |
| trans-HFC-1234ze/HFC-134/DME | 1-98/1-98/1-40 | 10-80/10-80/1-30 | |
| trans-HFC-1234ze/HFC-134a/HFC-152a | 1-98/1-98/1-98 | 10-80/10-80/1-50 | |
| trans-HFC-1234ze/HFC-152a/n-butane | 1-98/1-98/1-50 | 10-80/10-80/1-30 | |
| trans-HFC-1234ze/HFC-152a/DME | 1-98/1-98/1-98 | 20-90/1-50/1-30 | |
| trans-HFC-1234ze/HFC-227ea/n-butane | 1-98/1-98/1-40 | 10-80/10-80/1-30 | |
| trans-HFC-1234ze/n-butane/DME | 1-98/1-40/1-98 | 10-90/1-30/1-30 | |
| trans-HFC-1234ze/n-butane/CF$_3$I | 1-98/1-30/1-98 | 10-80/1-20/10-80 | |
| trans-HFC-1234ze/isobutane/DME | 1-98/1-60/1-98 | 10-90/1-30/1-30 | |
| trans-HFC-1234ze/isobutane/CF$_3$I | 1-98/1-40/1-98 | 10-80/1-20/10-80 | |
| trans-HFC-1234ze/isobutane/CF$_3$SCF$_3$ | 1-98/1-40/1-98 | 10-80/1-20/10-80 | |
| HFC-1243zf/HFC-134/HFC-227ea | 1-98/1-98/1-98 | 10-80/10-80/10-80 | |
| HFC-1243zf/HFC-134/n-butane | 1-98/1-98/1-40 | 10-80/10-80/1-30 | |
| HFC-1243zf/HFC-134/DME | 1-98/1-98/1-98 | 10-80/10-80/1-30 | |
| HFC-1243zf/HFC-134/CF$_3$I | 1-98/1-98/1-98 | 10-80/10-80/10-80 | |
| HFC-1243zf/HFC-134a/HFC-152a | 1-98/1-98/1-98 | 10-80/10-80/1-50 | |
| HFC-1243zf/HFC-134a/n-butane | 1-98/1-98/1-40 | 10-80/10-80/1-30 | |
| HFC-1243zf/HFC-152a/propane | 1-70/1-70/29-98 | 10-70/1-50/29-40 | |
| HFC-1243zf/HFC-152a/n-butane | 1-98/1-98/1-30 | 10-80/1-80/1-20 | |
| HFC-1243zf/HFC-152a/isobutane | 1-98/1-98/1-40 | 10-80/1-80/1-30 | |
| HFC-1243zf/HFC-152a/DME | 1-98/1-98/1-98 | 10-80/1-80/1-30 | |
| HFC-1243zf/HFC-227ea/n-butane | 1-98/1-98/1-40 | 10-80/1-80/1-30 | |
| HFC-1243zf/HFC-227ea/isobutane | 1-98/1-90/1-50 | 10-80/1-80/1-30 | |
| HFC-1243zf/HFC-227ea/DME | 1-98/1-80/1-90 | 10-80/1-80/1-30 | |
| HFC-1243zf/n-butane/DME | 1-98/1-40/1-98 | 10-90/1-30/1-30 | |
| HFC-1243zf/isobutane/DME | 1-98/1-60/1-98 | 10-90/1-30/1-30 | |
| HFC-1243zf/isobutane/CF$_3$I | 1-98/1-40/1-98 | 10-80/1-30/10-80 | |
| HFC-1243zf/DME/CF$_3$SCF$_3$ | 1-98/1-40/1-90 | 10-80/1-30/10-80 | |
| HFC-1225ye/HFC-32/CF$_3$I | 1-98/1-98/1-98 | 5-80/1-70/1-80 | |
| HFC-1225ye/HFC-1234yf/HFC-32/HFC-125 | 1-97/1-97/1-97/1-97 | 1-80/1-70/5-70/5-70 | |
| HFC-1225ye/HFC-1234yf/HFC-32/HFC-134a | 1-97/1-97/1-97/1-97 | 5-80/5-70/5-70/5-70 | |
| HFC-1225ye/HFC-1234yf/HFC-32/HFC-125/CF$_3$I | 1-96/1-96/1-96/1-96/1-96 | 1-70/1-60/1-70/1-60/1-60 | |
| HFC-1225ye/HFC-32/HFC-125/HFC-152a | 1-97/1-97/1-97/1-97 | 10-80/5-70/5-70/5-70 | |
| HFC-1225ye/HFC-32/HFC-125/isobutane | 1-97/1-97/1-97/1-97 | 5-70/5-70/5-70/1-30 | |
| HFC-1225ye/HFC-32/HFC-125/propane | 1-97/1-97/1-97/1-50 | 5-70/5-70/5-70/1-30 | |
| HFC-1225ye/HFC-32/HFC-125/DME | 1-97/1-97/1-97/1-50 | 5-70/5-70/5-70/1-30 | |
| HFC-1225ye/HFC-32/CF$_3$I/DME | 1-97/1-97/1-97/1-50 | 5-70/5-70/5-70/1-30 | |
| HFC-1225ye/HFC-32/HFC-125/CF$_3$I | 1-97/1-97/1-97/1-97 | 10-80/5-70/5-70/1-80 | |
| HFC-1234yf/HFC-32/CF$_3$I | 1-98/1-98/1-98 | 10-80/1-70/1-80 | |
| HFC-1234yf/HFC-32/HFC-134a/CF$_3$I | 1-97/1-97/1-97/1-97 | 5-70/5-80/1-70/5-70 | |
| HFC-1234yf/HFC-32/HFC-125 | 1-98/1-98/1-98 | 10-80/5-80/10-80 | |
| HFC-1234yf/HFC-32/HFC-125/CF$_3$I | 1-97/1-97/1-97/1-97 | 10-80/5-70/10-80/5-80 | |

The most preferred compositions of the present invention listed in Table 3 are generally expected to maintain the desired properties and functionality when the components are present in the concentrations as listed +/−2 weight percent. The compositions containing $CO_2$ would be expected to maintain the desired properties and functionality when the $CO_2$ was present at the listed concentration +/−0.2 weight percent.

The compositions of the present invention may be azeotropic or near-azeotropic compositions. By azeotropic composition is meant a constant-boiling mixture of two or more substances that behave as a single substance. One way to characterize an azeotropic composition is that the vapor produced by partial evaporation or distillation of the liquid has the same composition as the liquid from which it is evaporated or distilled, i.e., the mixture distills/refluxes without compositional change. Constant-boiling compositions are characterized as azeotropic because they exhibit either a maximum or minimum boiling point, as compared with that of the non-azeotropic mixture of the same compounds. An azeotropic composition will not fractionate within a refrigeration or air conditioning system during operation, which may reduce efficiency of the system. Additionally, an azeotropic composition will not fractionate upon leakage from a refrigeration or air conditioning system. In the situation where one component of a mixture is flammable, fractionation during leakage could lead to a flammable composition either within the system or outside of the system.

A near-azeotropic composition (also commonly referred to as an "azeotrope-like composition") is a substantially constant boiling liquid admixture of two or more substances that behaves essentially as a single substance. One way to characterize a near-azeotropic composition is that the vapor produced by partial evaporation or distillation of the liquid has substantially the same composition as the liquid from which it was evaporated or distilled, that is, the admixture distills/refluxes without substantial composition change. Another way to characterize a near-azeotropic composition is that the bubble point vapor pressure and the dew point vapor pressure of the composition at a particular temperature are substantially the same. Herein, a composition is near-azeotropic if, after 50 weight percent of the composition is removed, such as by evaporation or boiling off, the difference in vapor pressure between the original composition and the composition remaining after 50 weight percent of the original composition has been removed is less than about 10 percent.

Azeotropic compositions of the present invention at a specified temperature are shown in Table 4.

TABLE 4

| Component A | Component B | Wt % A | Wt % B | Psia | kPa | T (C.) |
|---|---|---|---|---|---|---|
| HFC-1234yf | HFC-32 | 7.4 | 92.6 | 49.2 | 339 | −25 |
| HFC-1234yf | HFC-125 | 10.9 | 89.1 | 40.7 | 281 | −25 |
| HFC-1234yf | HFC-134a | 70.4 | 29.6 | 18.4 | 127 | −25 |
| HFC-1234yf | HFC-152a | 91.0 | 9.0 | 17.9 | 123 | −25 |
| HFC-1234yf | HFC-143a | 17.3 | 82.7 | 39.5 | 272 | −25 |
| HFC-1234yf | HFC-227ea | 84.6 | 15.4 | 18.0 | 124 | −25 |
| HFC-1234yf | propane | 51.5 | 48.5 | 33.5 | 231 | −25 |
| HFC-1234yf | n-butane | 98.1 | 1.9 | 17.9 | 123 | −25 |
| HFC-1234yf | isobutane | 88.1 | 11.9 | 19.0 | 131 | −25 |
| HFC-1234yf | DME | 53.5 | 46.5 | 13.1 | 90 | −25 |
| HFC-1225ye | trans-HFC-1234ze | 63.0 | 37.0 | 11.7 | 81 | −25 |
| HFC-1225ye | HFC-1243zf | 40.0 | 60.0 | 13.6 | 94 | −25 |
| HFC-1225ye | HFC-134 | 52.2 | 47.8 | 12.8 | 88 | −25 |
| HFC-1225ye | HFC-152a | 7.3 | 92.7 | 14.5 | 100 | −25 |
| HFC-1225ye | propane | 29.7 | 70.3 | 30.3 | 209 | −25 |
| HFC-1225ye | n-butane | 89.5 | 10.5 | 12.3 | 85 | −25 |
| HFC-1225ye | isobutane | 79.3 | 20.7 | 13.9 | 96 | −25 |
| HFC-1225ye | DME | 82.1 | 17.9 | 10.8 | 74 | −25 |
| HFC-1225ye | $CF_3SCF_3$ | 37.0 | 63.0 | 12.4 | 85 | −25 |
| trans-HFC-1234ze | HFC-1243zf | 17.0 | 83.0 | 13.0 | 90 | −25 |
| trans-HFC-1234ze | HFC-134 | 45.7 | 54.3 | 12.5 | 86 | −25 |
| trans-HFC-1234ze | HFC-134a | 9.5 | 90.5 | 15.5 | 107 | −25 |
| trans-HFC-1234ze | HFC-152a | 21.6 | 78.4 | 14.6 | 101 | −25 |
| trans-HFC-1234ze | HFC-227ea | 59.2 | 40.8 | 11.7 | 81 | −25 |
| trans-HFC-1234ze | propane | 28.5 | 71.5 | 30.3 | 209 | −25 |
| trans-HFC-1234ze | n-butane | 88.6 | 11.4 | 11.9 | 82 | −25 |
| trans-HFC-1234ze | isobutane | 77.9 | 22.1 | 12.9 | 89 | −25 |
| trans-HFC-1234ze | DME | 84.1 | 15.9 | 10.8 | 74 | −25 |
| trans-HFC-1234ze | $CF_3SCF_3$ | 34.3 | 65.7 | 12.7 | 88 | −25 |
| HFC-1243zf | HFC-134 | 63.0 | 37.0 | 13.5 | 93 | −25 |
| HFC-1243zf | HFC-134A | 25.1 | 74.9 | 15.9 | 110 | −25 |
| HFC-1243zf | HFC-152A | 40.7 | 59.3 | 15.2 | 104 | −25 |
| HFC-1243zf | HFC-227ea | 78.5 | 21.5 | 13.1 | 90 | −25 |
| HFC-1243zf | propane | 32.8 | 67.2 | 31.0 | 213 | −25 |
| HFC-1243zf | n-butane | 90.3 | 9.7 | 13.5 | 93 | −25 |
| HFC-1243zf | isobutane | 80.7 | 19.3 | 14.3 | 98 | −25 |
| HFC-1243zf | DME | 72.7 | 27.3 | 12.0 | 83 | −25 |
| cis-HFC-1234ze | HFC-236ea | 20.9 | 79.1 | 30.3 | 209 | 25 |
| cis-HFC-1234ze | HFC-245fa | 76.2 | 23.8 | 26.1 | 180 | 25 |
| cis-HFC-1234ze | n-butane | 51.4 | 48.6 | 6.08 | 42 | −25 |
| cis-HFC-1234ze | isobutane | 26.2 | 73.8 | 8.74 | 60 | −25 |
| cis-HFC-1234ze | 2-methylbutane | 86.6 | 13.4 | 27.2 | 188 | 25 |
| cis-HFC-1234ze | n-pentane | 92.9 | 7.1 | 26.2 | 181 | 25 |
| HFC-1234ye | HFC-236ea | 24.0 | 76.0 | 3.35 | 23.1 | −25 |
| HFC-1234ye | HFC-245fa | 42.5 | 57.5 | 22.8 | 157 | 25 |
| HFC-1234ye | n-butane | 41.2 | 58.8 | 38.0 | 262 | 25 |
| HFC-1234ye | isobutane | 16.4 | 83.6 | 50.9 | 351 | 25 |

TABLE 4-continued

| Component A | Component B | Wt % A | Wt % B | Psia | kPa | T (C.) |
|---|---|---|---|---|---|---|
| HFC-1234ye | 2-methylbutane | 80.3 | 19.7 | 23.1 | 159 | 25 |
| HFC-1234ye | n-pentane | 87.7 | 12.3 | 21.8 | 150 | 25 |

Additionally, ternary azeotropes composition have been found as listed in Table 5.

TABLE 5

| Component A | Component B | Component C | Wt % A | Wt % B | Wt % C | Pres (psi) | Pres (kPa) | Temp (° C.) |
|---|---|---|---|---|---|---|---|---|
| HFC-1234yf | HFC-32 | HFC-143A | 3.9 | 74.3 | 21.8 | 50.02 | 345 | −25 |
| HFC-1234yf | HFC-32 | isobutane | 1.1 | 92.1 | 6.8 | 50.05 | 345 | −25 |
| HFC-1234yf | HFC-125 | HFC-143A | 14.4 | 43.5 | 42.1 | 38.62 | 266 | −25 |
| HFC-1234yf | HFC-125 | isobutane | 9.7 | 89.1 | 1.2 | 40.81 | 281 | −25 |
| HFC-1234yf | HFC-134 | propane | 4.3 | 39.1 | 56.7 | 34.30 | 236 | −25 |
| HFC-1234yf | HFC-134 | DME | 15.2 | 67.0 | 17.8 | 10.38 | 71.6 | −25 |
| HFC-1234yf | HFC-134a | propane | 24.5 | 31.1 | 44.5 | 34.01 | 234 | −25 |
| HFC-1234yf | HFC-134a | n-butane | 60.3 | 35.2 | 4.5 | 18.58 | 128 | −25 |
| HFC-1234yf | HFC-134a | isobutane | 48.6 | 37.2 | 14.3 | 19.86 | 137 | −25 |
| HFC-1234yf | HFC-134a | DME | 24.0 | 67.9 | 8.1 | 17.21 | 119 | −25 |
| HFC-1234yf | HFC-143a | propane | 17.7 | 71.0 | 11.3 | 40.42 | 279 | −25 |
| HFC-1234yf | HFC-143a | DME | 5.7 | 93.0 | 1.3 | 39.08 | 269 | −25 |
| HFC-1234yf | HFC-152a | n-butane | 86.6 | 10.8 | 2.7 | 17.97 | 124 | −25 |
| HFC-1234yf | HFC-152a | isobutane | 75.3 | 11.8 | 12.9 | 19.12 | 132 | −25 |
| HFC-1234yf | HFC-152a | DME | 24.6 | 43.3 | 32.1 | 11.78 | 81.2 | −25 |
| HFC-1234yf | HFC-227ea | propane | 35.6 | 17.8 | 46.7 | 33.84 | 233 | −25 |
| HFC-1234yf | HFC-227ea | n-butane | 81.9 | 16.0 | 2.1 | 18.07 | 125 | −25 |
| HFC-1234yf | HFC-227ea | isobutane | 70.2 | 18.2 | 11.6 | 19.27 | 133 | −25 |
| HFC-1234yf | HFC-227ea | DME | 28.3 | 55.6 | 16.1 | 15.02 | 104 | −25 |
| HFC-1234yf | n-butane | DME | 48.9 | 4.6 | 46.4 | 13.15 | 90.7 | −25 |
| HFC-1234yf | isobutane | DME | 31.2 | 26.2 | 42.6 | 14.19 | 97.8 | −25 |
| HFC-1234yf | DME | $CF_3I$ | 16.3 | 10.0 | 73.7 | 15.65 | 108 | −25 |
| HFC-1234yf | DME | $CF_3SCF_3$ | 34.3 | 10.5 | 55.2 | 14.57 | 100 | −25 |
| HFC-1225ye | trans-HFC-1234ze | HFC-134 | 47.4 | 5.6 | 47.0 | 12.77 | 88.0 | −25 |
| HFC-1225ye | trans-HFC-1234ze | HFC-227ea | 28.4 | 52.6 | 19.0 | 11.63 | 80.2 | −25 |
| HFC-1225ye | trans-HFC-1234ze | propane | 20.9 | 9.1 | 70.0 | 30.36 | 209 | −25 |
| HFC-1225ye | trans-HFC-1234ze | n-butane | 65.8 | 24.1 | 10.1 | 12.39 | 85.4 | −25 |
| HFC-1225ye | trans-HFC-1234ze | DME | 41.0 | 40.1 | 18.9 | 10.98 | 75.7 | −25 |
| HFC-1225ye | trans-HFC-1234ze | $CF_3SCF_3$ | 1.0 | 33.7 | 65.2 | 12.66 | 87.3 | −25 |
| HFC-1225ye | HFC-1243zf | HFC-134 | 28.7 | 47.3 | 24.1 | 13.80 | 95.1 | −25 |
| HFC-1225ye | HFC-1243zf | n-butane | 37.5 | 55.0 | 7.5 | 13.95 | 96.2 | −25 |
| HFC-1225ye | HFC-1243zf | isobutane | 40.5 | 43.2 | 16.3 | 14.83 | 102 | −25 |
| HFC-1225ye | HFC-1243zf | DME | 19.1 | 51.0 | 29.9 | 12.15 | 83.8 | −25 |
| HFC-1225ye | HFC-1243zf | $CF_3I$ | 10.3 | 27.3 | 62.3 | 14.05 | 96.9 | −25 |
| HFC-1225ye | HFC-134 | HFC-152a | 63.6 | 26.8 | 9.6 | 12.38 | 85.4 | −25 |
| HFC-1225ye | HFC-134 | HFC-227ea | 1.3 | 52.3 | 46.4 | 12.32 | 84.9 | −25 |
| HFC-1225ye | HFC-134 | n-butane | 18.1 | 67.1 | 14.9 | 14.54 | 100 | −25 |
| HFC-1225ye | HFC-134 | isobutane | 0.7 | 74.0 | 25.3 | 16.68 | 115 | −25 |
| HFC-1225ye | HFC-134 | DME | 29.8 | 52.5 | 17.8 | 9.78 | 67.4 | −25 |
| HFC-1225ye | HFC-227ea | DME | 63.1 | 31.0 | 5.8 | 10.93 | 75.4 | −25 |
| HFC-1225ye | n-butane | DME | 66.0 | 13.0 | 21.1 | 11.34 | 78.2 | −25 |
| HFC-1225ye | n-butane | $CF_3SCF_3$ | 71.3 | 5.6 | 23.0 | 12.25 | 84.5 | −25 |
| HFC-1225ye | isobutane | DME | 49.9 | 29.7 | 20.4 | 12.83 | 88.5 | −25 |
| HFC-1225ye | isobutane | $CF_3I$ | 27.7 | 2.2 | 70.1 | 13.19 | 90.9 | −25 |
| Trans-HFC-1234ze | HFC-1243zf | HFC-227ea | 7.1 | 73.7 | 19.2 | 13.11 | 90.4 | −25 |
| Trans-HFC-1234ze | HFC-1243zf | n-butane | 9.5 | 81.2 | 9.3 | 13.48 | 92.9 | −25 |
| Trans-HFC-1234ze | HFC-1243zf | isobutane | 3.3 | 77.6 | 19.1 | 14.26 | 98.3 | −25 |
| Trans-HFC-1234ze | HFC-1243zf | DME | 2.6 | 70.0 | 27.4 | 12.03 | 82.9 | −25 |
| Trans-HFC-1234ze | HFC-134 | HFC-152a | 52.0 | 42.9 | 5.1 | 12.37 | 85.3 | −25 |
| Trans-HFC-1234ze | HFC-134 | HFC-227ea | 30.0 | 43.2 | 26.8 | 12.61 | 86.9 | −25 |
| Trans-HFC-1234ze | HFC-134 | DME | 27.7 | 54.7 | 17.7 | 9.76 | 67.3 | −25 |

TABLE 5-continued

| Component A | Component B | Component C | Wt % A | Wt % B | Wt % C | Pres (psi) | Pres (kPa) | Temp (° C.) |
|---|---|---|---|---|---|---|---|---|
| Trans-HFC-1234ze | HFC-134a | HFC-152a | 14.4 | 34.7 | 51.0 | 14.42 | 99.4 | −25 |
| Trans-HFC-1234ze | HFC-152a | n-butane | 5.4 | 80.5 | 14.1 | 15.41 | 106 | −25 |
| Trans-HFC-1234ze | HFC-152a | DME | 59.1 | 16.4 | 24.5 | 10.80 | 74.5 | −25 |
| Trans-HFC-1234ze | HFC-227ea | n-butane | 40.1 | 48.5 | 11.3 | 12.61 | 86.9 | −25 |
| Trans-HFC-1234ze | n-butane | DME | 68.1 | 13.0 | 18.9 | 11.29 | 77.8 | −25 |
| Trans-HFC-1234ze | n-butane | $CF_3I$ | 81.2 | 9.7 | 9.1 | 11.87 | 81.8 | −25 |
| Trans-HFC-1234ze | isobutane | DME | 55.5 | 28.7 | 15.8 | 12.38 | 85.4 | −25 |
| Trans-HFC-1234ze | isobutane | $CF_3I$ | 34.9 | 6.1 | 59.0 | 12.57 | 86.7 | −25 |
| Trans-HFC-1234ze | isobutane | $CF_3SCF_3$ | 37.7 | 1.1 | 61.7 | 12.66 | 87.3 | −25 |
| HFC-1243zf | HFC-134 | HFC-227ea | 58.6 | 34.1 | 7.3 | 13.54 | 93.4 | −25 |
| HFC-1243zf | HFC-134 | n-butane | 27.5 | 58.7 | 13.9 | 14.72 | 101 | −25 |
| HFC-1243zf | HFC-134 | DME | 18.7 | 63.5 | 17.8 | 10.11 | 69.7 | −25 |
| HFC-1243zf | HFC-134 | $CF_3I$ | 11.4 | 23.9 | 64.7 | 14.45 | 99.6 | −25 |
| HFC-1243zf | HFC-134a | HFC-152a | 41.5 | 21.5 | 37.1 | 14.95 | 103 | −25 |
| HFC-1243zf | HFC-134A | n-butane | 7.0 | 81.4 | 11.6 | 17.03 | 117 | −25 |
| HFC-1243zf | HFC-152a | propane | 2.9 | 34.0 | 63.0 | 31.73 | 219 | −25 |
| HFC-1243zf | HFC-152a | n-butane | 28.8 | 60.3 | 11.0 | 15.71 | 108 | −25 |
| HFC-1243zf | HFC-152a | isobutane | 6.2 | 68.5 | 25.3 | 17.05 | 118 | −25 |
| HFC-1243zf | HFC-152a | DME | 33.1 | 36.8 | 30.1 | 11.41 | 78.7 | −25 |
| HFC-1243zf | HFC-227ea | n-butane | 62.0 | 28.4 | 9.6 | 13.67 | 94.3 | −25 |
| HFC-1243zf | HFC-227ea | isobutane | 27.9 | 51.0 | 21.1 | 15.00 | 103 | −25 |
| HFC-1243zf | HFC-227ea | DME | 48.1 | 44.8 | 7.2 | 12.78 | 88.1 | −25 |
| HFC-1243zf | n-butane | DME | 60.3 | 10.1 | 29.6 | 12.28 | 84.7 | −25 |
| HFC-1243zf | isobutane | DME | 47.1 | 26.9 | 25.9 | 13.16 | 90.7 | −25 |
| HFC-1243zf | isobutane | $CF_3I$ | 32.8 | 1.1 | 66.1 | 13.97 | 96.3 | −25 |
| HFC-1243zf | DME | $CF_3SCF_3$ | 41.1 | 2.3 | 56.6 | 13.60 | 93.8 | −25 |

The near-azeotropic compositions of the present invention at a specified temperature are listed in Table 6.

TABLE 6

| Component A | Component B | (wt % A/wt % B) | T (C.) |
|---|---|---|---|
| HFC-1234yf | HFC-32 | 1-57/99-43 | −25 |
| HFC-1234yf | HFC-125 | 1-51/99-49 | −25 |
| HFC-1234yf | HFC-134 | 1-99/99-1 | −25 |
| HFC-1234yf | HFC-134a | 1-99/99-1 | −25 |
| HFC-1234yf | HFC-152a | 1-99/99-1 | −25 |
| HFC-1234yf | HFC-161 | 1-99/99-1 | −25 |
| HFC-1234yf | HFC-143a | 1-60/99-40 | −25 |
| HFC-1234yf | HFC-227ea | 29-99/71-1 | −25 |
| HFC-1234yf | HFC-236fa | 66-99/34-1 | −25 |
| HFC-1234yf | HFC-1225ye | 1-99/99-1 | −25 |
| HFC-1234yf | trans-HFC-1234ze | 1-99/99-1 | −25 |
| HFC-1234yf | HFC-1243zf | 1-99/99-1 | −25 |
| HFC-1234yf | propane | 1-80/99-20 | −25 |
| HFC-1234yf | n-butane | 71-99/29-1 | −25 |
| HFC-1234yf | isobutane | 60-99/40-1 | −25 |
| HFC-1234yf | DME | 1-99/99-1 | −25 |
| HFC-1225ye | trans-HFC-1234ze | 1-99/99-1 | −25 |
| HFC-1225ye | HFC-1243zf | 1-99/99-1 | −25 |
| HFC-1225ye | HFC-134 | 1-99/99-1 | −25 |
| HFC-1225ye | HFC-134a | 1-99/99-1 | −25 |
| HFC-1225ye | HFC-152a | 1-99/99-1 | −25 |
| HFC-1225ye | HFC-161 | 1-84/99-16, 90-99/10-1 | −25 |
| HFC-1225ye | HFC-227ea | 1-99/99-1 | −25 |
| HFC-1225ye | HFC-236ea | 57-99/43-1 | −25 |
| HFC-1225ye | HFC-236fa | 48-99/52-1 | −25 |
| HFC-1225ye | HFC-245fa | 70-99/30-1 | −25 |
| HFC-1225ye | propane | 1-72/99-28 | −25 |
| HFC-1225ye | n-butane | 65-99/35-1 | −25 |
| HFC-1225ye | isobutane | 50-99/50-1 | −25 |
| HFC-1225ye | DME | 1-99/99-1 | −25 |
| HFC-1225ye | $CF_3I$ | 1-99/99-1 | −25 |
| HFC-1225ye | $CF_3SCF_3$ | 1-99/99-1 | −25 |
| trans-HFC-1234ze | cis-HFC-1234ze | 73-99/27-1 | −25 |
| trans-HFC-1234ze | HFC-1243zf | 1-99/99-1 | −25 |
| trans-HFC-1234ze | HFC-134 | 1-99/99-1 | −25 |
| trans-HFC-1234ze | HFC-134a | 1-99/99-1 | −25 |
| trans-HFC-1234ze | HFC-152a | 1-99/99-1 | −25 |
| trans-HFC-1234ze | HFC-161 | 1-52/99-48, 87-99/13-1 | −25 |
| trans-HFC-1234ze | HFC-227ea | 1-99/99-1 | −25 |
| trans-HFC-1234ze | HFC-236ea | 54-99/46-1 | −25 |
| trans-HFC-1234ze | HFC-236fa | 44-99/56-1 | −25 |
| trans-HFC-1234ze | HFC-245fa | 67-99/33-1 | −25 |
| trans-HFC-1234ze | propane | 1-71/99-29 | −25 |
| trans-HFC-1234ze | n-butane | 62-99/38-1 | −25 |
| trans-HFC-1234ze | isobutane | 39-99/61-1 | −25 |
| trans-HFC-1234ze | DME | 1-99/99-1 | −25 |
| trans-HFC-1234ze | $CF_3SCF_3$ | 1-99/99-1 | −25 |
| trans-HFC-1234ze | $CF_3I$ | 1-99/99-1 | −25 |
| HFC-1243zf | HFC-134 | 1-99/99-1 | −25 |
| HFC-1243zf | HFC-134a | 1-99/99-1 | −25 |
| HFC-1243zf | HFC-152a | 1-99/99-1 | −25 |
| HFC-1243zf | HFC-161 | 1-99/99-1 | −25 |
| HFC-1243zf | HFC-227ea | 1-99/99-1 | −25 |
| HFC-1243zf | HFC-236ea | 53-99/47-1 | −25 |
| HFC-1243zf | HFC-236fa | 49-99/51-1 | −25 |
| HFC-1243zf | HFC-245fa | 66-99/34-1 | −25 |
| HFC-1243zf | propane | 1-71/99-29 | −25 |
| HFC-1243zf | n-butane | 62-99/38-1 | −25 |
| HFC-1243zf | isobutane | 45-99/55-1 | −25 |
| HFC-1243zf | DME | 1-99/99-1 | −25 |
| cis-HFC-1234ze | HFC-236ea | 1-99/99-1 | 25 |
| cis-HFC-1234ze | HFC-236fa | 1-99/99-1 | 25 |
| cis-HFC-1234ze | HFC-245fa | 1-99/99-1 | 25 |

TABLE 6-continued

| Component A | Component B | (wt % A/wt % B) | T (C.) |
|---|---|---|---|
| cis-HFC-1234ze | n-butane | 1-80/99-20 | −25 |
| cis-HFC-1234ze | isobutane | 1-69/99-31 | −25 |
| cis-HFC-1234ze | 2-methylbutane | 60-99/40-1 | 25 |
| cis-HFC-1234ze | n-pentane | 63-99/37-1 | 25 |
| HFC-1234ye | HFC-134 | 38-99/62-1 | 25 |
| HFC-1234ye | HFC-236ea | 1-99/99-1 | −25 |
| HFC-1234ye | HFC-236fa | 1-99/99-1 | 25 |
| HFC-1234ye | HFC-245fa | 1-99/99-1 | 25 |
| HFC-1234ye | Cis-HFC-1234ze | 1-99/99-1 | 25 |
| HFC-1234ye | n-butane | 1-78/99-22 | 25 |
| HFC-1234ye | cyclopentane | 70-99/30-1 | 25 |
| HFC-1234ye | isobutane | 1-68/99-32 | 25 |
| HFC-1234ye | 2-methylbutane | 47-99/53-1 | 25 |
| HFC-1234ye | n-pentane | 57-99/43-1 | 25 |

Ternary and higher order near-azeotrope compositions comprising fluoroolefins have also been identified as listed in Table 7.

TABLE 7

| Components | Near-azeotrope range (weight percent) | Temp (° C.) |
|---|---|---|
| HFC-1225ye/HFC-134a/HFC-152a | 1-98/1-98/1-98 | 25 |
| HFC-1225ye/HFC-134a/HFC-161 | 1-98/1-98/1-98 | 25 |
| HFC-1225ye/HFC-134a/isobutane | 1-98/1-98/1-40 | 25 |
| HFC-1225ye/HFC-134a/DME | 1-98/1-98/1-20 | 25 |
| HFC-1225ye/HFC-152a/isobutane | 1-98/1-98/1-50 | 25 |
| HFC-1225ye/HFC-152a/DME | 1-98/1-98/1-98 | 25 |
| HFC-1225ye/HFC-1234yf/HFC-134a | 1-98/1-98/1-98 | 25 |
| HFC-1225ye/HFC-1234yf/HFC-152a | 1-98/1-98/1-98 | 25 |
| HFC-1225ye/HFC-1234yf/HFC-125 | 1-98/1-98/1-20 | 25 |
| HFC-1225ye/HFC-1234yf/CF$_3$I | 1-98/1-98/1-98 | 25 |
| HFC-1225ye/HFC-134a/HFC-152a/HFC-32 | 1-97/1-97/1-97/1-10 | 25 |
| HFC-125/HFC-1225ye/isobutane | 80-98/1-19/1-10 | 25 |
| HFC-125/trans-HFC-1234ze/isobutane | 80-98/1-19/1-10 | 25 |
| HFC-125/HFC-1234yf/isobutane | 80-98/1-19/1-10 | 25 |
| HFC-32/HFC-125/HFC-1225ye | 1-98/1-98/1-4 | 25 |
| HFC-32/HFC-125/trans-HFC-1234ze | 1-98/1-98/1-50 | 25 |
| HFC-32/HFC-125/HFC-1234yf | 1-98/1-98/1-55 | 25 |
| HFC-125/trans-HFC-1234ze/n-butane | 80-98/1-19/1-10 | 25 |
| HFC-125/HFC-1234yf/n-butane | 80-98/1-19/1-10 | 25 |
| HFC-1234yf/HFC-32/HFC-143a | 1-50/1-98/1-98 | −25 |
| HFC-1234yf/HFC-32/isobutane | 1-40/59-98/1-30 | −25 |
| HFC-1234yf/HFC-125/HFC-143a | 1-60/1-98/1-98 | −25 |
| HFC-1234yf/HFC-125/isobutane | 1-40/59-98/1-20 | −25 |
| HFC-1234yf/HFC-134/propane | 1-80/1-70/19-90 | −25 |
| HFC-1234yf/HFC-134/DME | 1-70/1-98/29-98 | −25 |
| HFC-1234yf/HFC-134a/propane | 1-80/1-80/19-98 | −25 |
| HFC-1234yf/HFC-134a/n-butane | 1-98/1-98/1-30 | −25 |
| HFC-1234yf/HFC-134a/isobutane | 1-98/1-98/1-30 | −25 |
| HFC-1234yf/HFC-134a/DME | 1-98/1-98/1-40 | −25 |
| HFC-1234yf/HFC-143a/propane | 1-80/1-98/1-98 | −25 |
| HFC-1234yf/HFC-143a/DME | 1-40/59-98/1-20 | −25 |
| HFC-1234yf/HFC-152a/n-butane | 1-98/1-98/1-30 | −25 |
| HFC-1234yf/HFC-152a/isobutane | 1-98/1-90/1-40 | −25 |
| HFC-1234yf/HFC-152a/DME | 1-70/1-98/1-98 | −25 |
| HFC-1234yf/HFC-227ea/propane | 1-80/1-70/29-98 | −25 |
| HFC-1234yf/HFC-227ea/n-butane | 40-98/1-59/1-20 | −25 |
| HFC-1234yf/HFC-227ea/isobutane | 30-98/1-69/1-30 | −25 |
| HFC-1234yf/HFC-227ea/DME | 1-98/1-80/1-98 | −25 |
| HFC-1234yf/n-butane/DME | 1-98/1-40/1-98 | −25 |
| HFC-1234yf/isobutane/DME | 1-98/1-50/1-98 | −25 |
| HFC-1234yf/DME/CF$_3$I | 1-98/1-98/1-98 | −25 |
| HFC-1234yf/DME/CF$_3$SCF$_3$ | 1-98/1-40/1-80 | −25 |
| HFC-1225ye/trans-HFC-1234ze/HFC-134 | 1-98/1-98/1-98 | −25 |
| HFC-1225ye/trans-HFC-1234ze/HFC-227ea | 1-98/1-98/1-98 | −25 |
| HFC-1225ye/trans-HFC-1234ze/propane | 1-60/1-60/1-98 | −25 |
| HFC-1225ye/trans-HFC-1234ze/n-butane | 1-98/1-98/1-30 | −25 |
| HFC-1225ye/trans-HFC-1234ze/DME | 1-98/1-98/1-98 | −25 |
| HFC-1225ye/trans-HFC-1234ze/CF$_3$SCF$_3$ | 1-98/1-98/1-98 | −25 |
| HFC-1225ye/HFC-1243zf/HFC-134 | 1-98/1-98/1-98 | −25 |
| HFC-1225ye/HFC-1243zf/n-butane | 1-98/1-98/1-30 | −25 |
| HFC-1225ye/HFC-1243zf/isobutane | 1-98/1-98/1-40 | −25 |
| HFC-1225ye/HFC-1243zf/DME | 1-98/1-98/1-98 | −25 |
| HFC-1225ye/HFC-1243zf/CF$_3$I | 1-98/1-98/1-98 | −25 |
| HFC-1225ye/HFC-134/HFC-152a | 1-98/1-98/1-98 | −25 |
| HFC-1225ye/HFC-134/HFC-227ea | 1-98/1-98/1-98 | −25 |
| HFC-1225ye/HFC-134/n-butane | 1-98/1-90/1-40 | −25 |
| HFC-1225ye/HFC-134/isobutane | 1-98/1-90/1-40 | −25 |
| HFC-1225ye/HFC-134/DME | 1-98/1-98/1-40 | −25 |
| HFC-1225ye/HFC-227ea/DME | 40-98/1-59/1-30 | −25 |
| HFC-1225ye/n-butane/DME | 1-98/1-30/1-98 | −25 |
| HFC-1225ye/n-butane/CF$_3$SCF$_3$ | 1-98/1-20/1-98 | −25 |
| HFC-1225ye/isobutane/DME | 1-98/1-60/1-98 | −25 |
| HFC-1225ye/isobutane/CF$_3$I | 1-98/1-40/1-98 | −25 |
| trans-HFC-1234ze/HFC-1243zf/HFC-227ea | 1-98/1-98/1-98 | −25 |
| trans-HFC-1234ze/HFC-1243zf/n-butane | 1-98/1-98/1-30 | −25 |
| trans-HFC-1234ze/HFC-1243zf/isobutane | 1-98/1-98/1-40 | −25 |
| trans-HFC-1234ze/HFC-1243zf/DME | 1-98/1-98/1-98 | −25 |
| trans-HFC-1234ze/HFC-134/HFC-152a | 1-98/1-98/1-98 | −25 |
| trans-HFC-1234ze/HFC-134/HFC-227ea | 1-98/1-98/1-98 | −25 |
| trans-HFC-1234ze/HFC-134/DME | 1-98/1-98/1-40 | −25 |
| trans-HFC-1234ze/HFC-134a/HFC-152a | 1-98/1-98/1-98 | −25 |
| trans-HFC-1234ze/HFC-152a/n-butane | 1-98/1-98/1-50 | −25 |
| trans-HFC-1234ze/HFC-152a/DME | 1-98/1-98/1-98 | −25 |
| trans-HFC-1234ze/HFC-227ea/n-butane | 1-98/1-98/1-40 | −25 |
| trans-HFC-1234ze/n-butane/DME | 1-98/1-40/1-98 | −25 |
| trans-HFC-1234ze/n-butane/CF$_3$I | 1-98/1-30/1-98 | −25 |
| trans-HFC-1234ze/isobutane/DME | 1-98/1-60/1-98 | −25 |
| trans-HFC-1234ze/isobutane/CF$_3$I | 1-98/1-40/1-98 | −25 |
| trans-HFC-1234ze/isobutane/CF$_3$SCF$_3$ | 1-98/1-40/1-98 | −25 |
| HFC-1243zf/HFC-134/HFC-227ea | 1-98/1-98/1-98 | −25 |
| HFC-1243zf/HFC-134/n-butane | 1-98/1-98/1-40 | −25 |
| HFC-1243zf/HFC-134/DME | 1-98/1-98/1-98 | −25 |
| HFC-1243zf/HFC-134/CF$_3$I | 1-98/1-98/1-98 | −25 |
| HFC-1243zf/HFC-134a/HFC-152a | 1-98/1-98/1-98 | −25 |
| HFC-1243zf/HFC-134a/n-butane | 1-98/1-98/1-40 | −25 |
| HFC-1243zf/HFC-152a/propane | 1-70/1-70/29-98 | −25 |
| HFC-1243zf/HFC-152a/n-butane | 1-98/1-98/1-30 | −25 |
| HFC-1243zf/HFC-152a/isobutane | 1-98/1-98/1-40 | −25 |
| HFC-1243zf/HFC-152a/DME | 1-98/1-98/1-98 | −25 |
| HFC-1243zf/HFC-227ea/n-butane | 1-98/1-98/1-40 | −25 |
| HFC-1243zf/HFC-227ea/isobutane | 1-98/1-90/1-50 | −25 |
| HFC-1243zf/HFC-227ea/DME | 1-98/1-80/1-90 | −25 |
| HFC-1243zf/n-butane/DME | 1-98/1-40/1-98 | −25 |
| HFC-1243zf/isobutane/DME | 1-98/1-60/1-98 | −25 |
| HFC-1243zf/isobutane/CF$_3$I | 1-98/1-40/1-98 | −25 |
| HFC-1243zf/DME/CF$_3$SCF$_3$ | 1-98/1-40/1-90 | −25 |

Additional compositions comprising fluoroolefins as disclosed in U.S. patent application Ser. No. 11/369,227 filed Mar. 2, 2006; U.S. patent application Ser. No. 11/393,109 filed Mar. 30, 2006; and U.S. patent application Ser. No. 11/486,791 filed Jul. 13, 2006; are intended to be included within the scope of the present invention.

Certain of the compositions of the present invention are non-azeotropic compositions. Those compositions of the present invention falling within the preferred ranges of Table 3, but outside of the near-azeotropic ranges of Table 6 and Table 7 may be considered to be non-azeotropic.

A non-azeotropic composition may have certain advantages over azeotropic or near azeotropic mixtures. A non-azeotropic composition is a mixture of two or more substances that behaves as a mixture rather than a single substance. One way to characterize a non-azeotropic composition is that the vapor produced by partial evaporation or distillation of the liquid has a substantially different composition as the liquid from which it was evaporated or distilled, that is, the admixture distills/refluxes with substantial composition change. Another way to characterize a non-azeotropic composition is that the bubble point vapor pressure and the dew point vapor pressure of the composition at a particular temperature are substantially different. Herein, a composition is non-azeotropic if, after 50 weight percent of the composition is removed, such as by evaporation or boiling off, the difference in vapor pressure between the original composition and the composition remaining after 50 weight percent of the original composition has been removed is greater than about 10 percent.

The compositions of the present invention may be prepared by any convenient method to combine the desired amounts of the individual components. A preferred method is to weigh the desired component amounts and thereafter combine the components in an appropriate vessel. Agitation may be used, if desired.

An alternative means for making compositions of the present invention may be a method for making a refrigerant blend composition, wherein said refrigerant blend composition comprises a composition as disclosed herein, said method comprising (i) reclaiming a volume of one or more components of a refrigerant composition from at least one refrigerant container, (ii) removing impurities sufficiently to enable reuse of said one or more of the reclaimed components, (iii) and optionally, combining all or part of said reclaimed volume of components with at least one additional refrigerant composition or component.

A refrigerant container may be any container in which is stored a refrigerant blend composition that has been used in a refrigeration apparatus, air-conditioning apparatus or heat pump apparatus. Said refrigerant container may be the refrigeration apparatus, air-conditioning apparatus or heat pump apparatus in which the refrigerant blend was used. Additionally, the refrigerant container may be a storage container for collecting reclaimed refrigerant blend components, including but not limited to pressurized gas cylinders.

Residual refrigerant means any amount of refrigerant blend or refrigerant blend component that may be moved out of the refrigerant container by any method known for transferring refrigerant blends or refrigerant blend components.

Impurities may be any component that is in the refrigerant blend or refrigerant blend component due to its use in a refrigeration apparatus, air-conditioning apparatus or heat pump apparatus. Such impurities include but are not limited to refrigeration lubricants, being those described earlier herein, particulates including but not limited to metal, metal salt or elastomer particles, that may have come out of the refrigeration apparatus, air-conditioning apparatus or heat pump apparatus, and any other contaminants that may adversely effect the performance of the refrigerant blend composition.

Such impurities may be removed sufficiently to allow reuse of the refrigerant blend or refrigerant blend component without adversely effecting the performance or equipment within which the refrigerant blend or refrigerant blend component will be used.

It may be necessary to provide additional refrigerant blend or refrigerant blend component to the residual refrigerant blend or refrigerant blend component in order to produce a composition that meets the specifications required for a given product. For instance, if a refrigerant blend has 3 components in a particular weight percentage range, it may be necessary to add one or more of the components in a given amount in order to restore the composition to within the specification limits.

The heat transfer fluid compositions of the present invention will have global warming potential (GWP) that are less than many hydrofluorocarbon refrigerants currently in use. Preferably, such compositions will also have zero or low ozone depletion potential. One aspect of the present invention is to provide a refrigerant with a global warming potential of less than 1000, less than 500, less than 150, less than 100, or less than 50. Another aspect of the present invention is to reduce the net GWP of refrigerant mixtures by adding fluoroolefins to said mixtures.

The compositions of the present invention may be useful as low global warming potential (GWP) replacements for currently used refrigerants, including but not limited to R134a (or HFC-134a, 1,1,1,2-tetrafluoroethane), R22 (or HCFC-22, chlorodifluoromethane), R123 (or HFC-123, 2,2-dichloro-1,1,1-trifluoroethane), R11 (CFC-11, fluorotrichloromethane), R12 (CFC-12, dichlorodifluoromethane), R245fa (or HFC-245fa, 1,1,1,3,3-pentafluoropropane), R114 (or CFC-114, 1,2-dichloro-1,1,2,2-tetrafluoroethane), R236fa (or HFC-236fa, 1,1,1,3,3,3-hexafluoropropane), R124 (or HCFC-124, 2-chloro-1,1,1,2-tetrafluoroethane), R407C (ASHRAE designation for a blend of 52 weight percent R134a, 25 weight percent R125 (pentafluoroethane), and 23 weight percent R32 (difluoromethane), R410A (ASHRAE designation for a blend of 50 weight percent R125 and 50 weight percent R32), R417A, (ASHRAE designation for a blend of 46.6 weight percent R125, 50.0 weight percent R134a, and 3.4 weight percent n-butane), R422A, R422B, R422c and R422D, (ASHRAE designation for a blend of 85.1 weight percent R125, 11.5 weight percent R134a, and 3.4 weight percent isobutane), R404A, (ASHRAE designation for a blend of 44 weight percent R125, 52 weight percent R143a (1,1,1-trifluoroethane), and 4.0 weight percent R134a) and R507A (ASHRAE designation for a blend of 50 weight percent R125 and 50 weight percent R143a). Additionally, the compositions of the present invention may be useful as replacements for R12 (CFC-12, dichlorodifluoromethane) or R502 (ASHRAE designation for a blend of 51.2 weight percent CFC-115 (chloropentafluoroethane) and 48.8 weight percent HCFC-22).

Often replacement refrigerants are most useful if capable of being used in the original refrigeration equipment designed for a different refrigerant. The compositions of the present invention may be useful as replacements for the above-mentioned refrigerants in original equipment. Additionally, the compositions of the present invention may be useful as replacements for the above mentioned refrigerants in equipment designed to use the above-mentioned refrigerants.

The compositions of the present invention may further comprise a lubricant. Lubricants of the present invention comprise refrigeration lubricants, i.e. those lubricants suitable for use with refrigeration, air-conditioning, or heat pump apparatus. Among these lubricants are those conventionally used in compression refrigeration apparatus utilizing chlorofluorocarbon refrigerants. Such lubricants and their properties are discussed in the 1990 ASHRAE Handbook, Refrigeration Systems and Applications, chapter 8, titled "Lubricants in Refrigeration Systems", pages 8.1 through 8.21. Lubricants of the present invention may comprise those commonly known as "mineral oils" in the field of compression refrigeration lubrication. Mineral oils comprise paraffins (i.e. straight-chain and branched-carbon-chain, saturated hydrocarbons), naphthenes (i.e. cyclic paraffins) and aromatics (i.e. unsaturated, cyclic hydrocarbons containing one or more rings characterized by alternating double bonds). Lubricants of the present invention further comprise those commonly known as "synthetic oils" in the field of compression refrigeration lubrication. Synthetic oils comprise alkylaryls (i.e. linear and branched alkyl alkylbenzenes), synthetic paraffins and napthenes, and poly(alphaolefins). Representative conventional lubricants of the present invention are the commercially available BVM 100 N (paraffinic mineral oil sold by BVA Oils), Suniso® 3GS and Suniso® 5GS (naphthenic mineral oil sold by Crompton Co.), Sontex® 372LT (naphthenic mineral oil sold by Pennzoil), Calumet® RO-30 (naphthenic mineral oil sold by Calumet Lubricants), Zerol® 75, Zerol® 150 and Zerol® 500 (linear alkylbenzenes sold by Shrieve Chemicals) and HAB 22 (branched alkylbenzene sold by Nippon Oil).

Lubricants of the present invention further comprise those that have been designed for use with hydrofluorocarbon refrigerants and are miscible with refrigerants of the present invention under compression refrigeration, air-conditioning, or heat pump apparatus' operating conditions. Such lubricants and their properties are discussed in "Synthetic Lubricants and High-Performance Fluids", R. L. Shubkin, editor, Marcel Dekker, 1993. Such lubricants include, but are not limited to, polyol esters (POEs) such as Castrol® 100 (Castrol, United Kingdom), polyalkylene glycols (PAGs) such as RL-488A from Dow (Dow Chemical, Midland, Mich.), and polyvinyl ethers (PVEs). These lubricants are readily available from various commercial sources.

Lubricants of the present invention are selected by considering a given compressor's requirements and the environment to which the lubricant will be exposed. Lubricants of the present invention preferably have a kinematic viscosity of at least about 5 cs (centistokes) at 40° C.

Commonly used refrigeration system additives may optionally be added, as desired, to compositions of the present invention in order to enhance lubricity and system stability. These additives are generally known within the field of refrigeration compressor lubrication, and include anti wear agents, extreme pressure lubricants, corrosion and oxidation inhibitors, metal surface deactivators, free radical scavengers, foaming and antifoam control agents, leak detectants and the like. In general, these additives are present only in small amounts relative to the overall lubricant composition. They are typically used at concentrations of from less than about 0.1% to as much as about 3% of each additive. These additives are selected on the basis of the individual system requirements. Some typical examples of such additives may include, but are not limited to, lubrication enhancing additives, such as alkyl or aryl esters of phosphoric acid and of thiophosphates. Additionally, the metal dialkyl dithiophosphates (e.g. zinc dialkyl dithiophosphate or ZDDP, Lubrizol 1375) and other members of this family of chemicals may be used in compositions of the present invention. Other antiwear additives include natural product oils and asymmetrical polyhydroxyl lubrication additives such as Synergol TMS (international Lubricants). Similarly, stabilizers such as anti oxidants, free radical scavengers, and water scavengers may be employed. Compounds in this category can include, but are not limited to, butylated hydroxy toluene (BHT) and epoxides.

The compositions of the present invention may further comprise about 0.01 weight percent to about 5 weight percent of an additive such as, for example, a stabilizer, free radical scavenger and/or antioxidant. Such additives include but are not limited to, nitromethane, hindered phenols, hydroxylamines, thiols, phosphites, or lactones. Single additives or combinations may be used.

The compositions of the present invention may further comprise about 0.01 weight percent to about 5 weight percent of a water scavenger (drying compound). Such water scavengers may comprise ortho esters such as trimethyl-, triethyl-, or tripropylortho formate.

In one embodiment, the present composition comprising a fluoroolefin may further comprises at least one compound selected from the group consisting of: HFC-1225ye, HFC-1234ze, HFC-1234yf, HFC-1234ye, HFC-1243zf, HFC-32, HFC-125, HFC-134, HFC-134a, HFC-143a, HFC-152a, HFC-161, HFC-227ea, HFC-236ea, HFC-236fa, HFC-245fa, HFC-365mfc, propane, n-butane, isobutane, 2-methylbutane, n-pentane, cyclopentane, dimethylether, $CF_3SCF_3$, $CO_2$, ammonia, and $CF_3I$.

The fluoroolefin compositions of the present invention are more easily detected at low levels as compared to the more conventional saturated fluorocarbon working fluids by virtue of the double bond. Therefore, with the present invention, no tracer type compound such as a dye is needed to detect the leakage, even at a low concentration level such as would be produced by a small leak site.

In another embodiment, the present invention provides a method for detecting a leak in a refrigeration or air-conditioning system wherein the refrigerant fluid comprises carbon dioxide, said method comprising adding a small amount of fluoroolefin to said refrigerant fluid. This inventive method makes it possible to detect a leak or carbon dioxide from the system even in the presence of ambient carbon dioxide in the air. The sensors of the present invention will respond to the fluoroolefin thus signaling that a leak is present. For the addition of fluoroolefin to be effective in the present method for detecting a leak of carbon dioxide, the fluoroolefin may be present at less than about 1 weight percent. In another embodiment, the fluoroolefin may be present in the range of about 0.1 weight percent (or 1000 ppm by weight) to about 0.01 weight percent (or 100 ppm by weight).

Example

Near-Infrared Spectrum for Fluoroolefin

Figure 2:
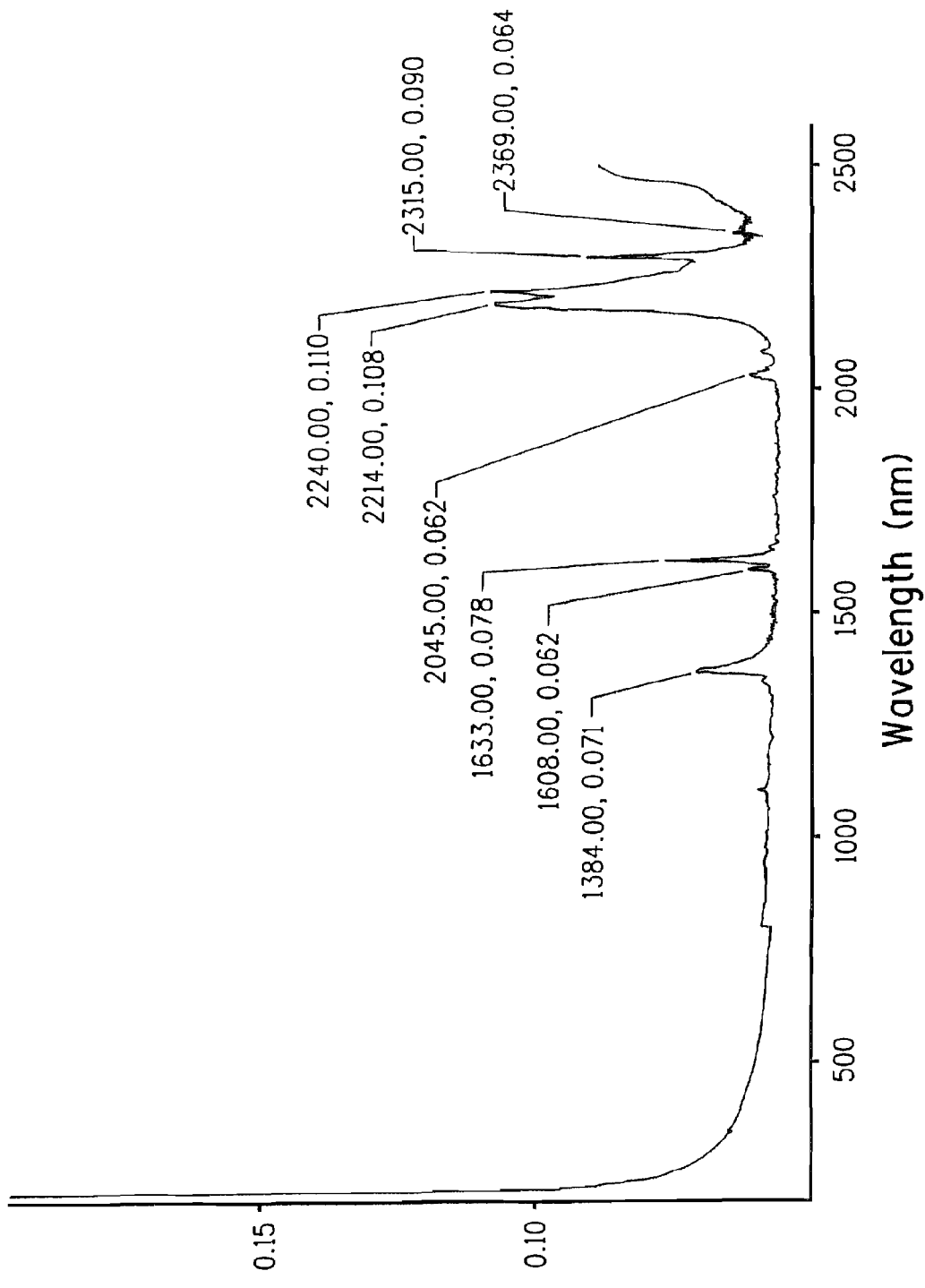
FIG. 2 shows the raw NIR spectral data for a sample of 1,2,3,3,3-pentafluoropropene (HFC-1225ye).
Figure 3:
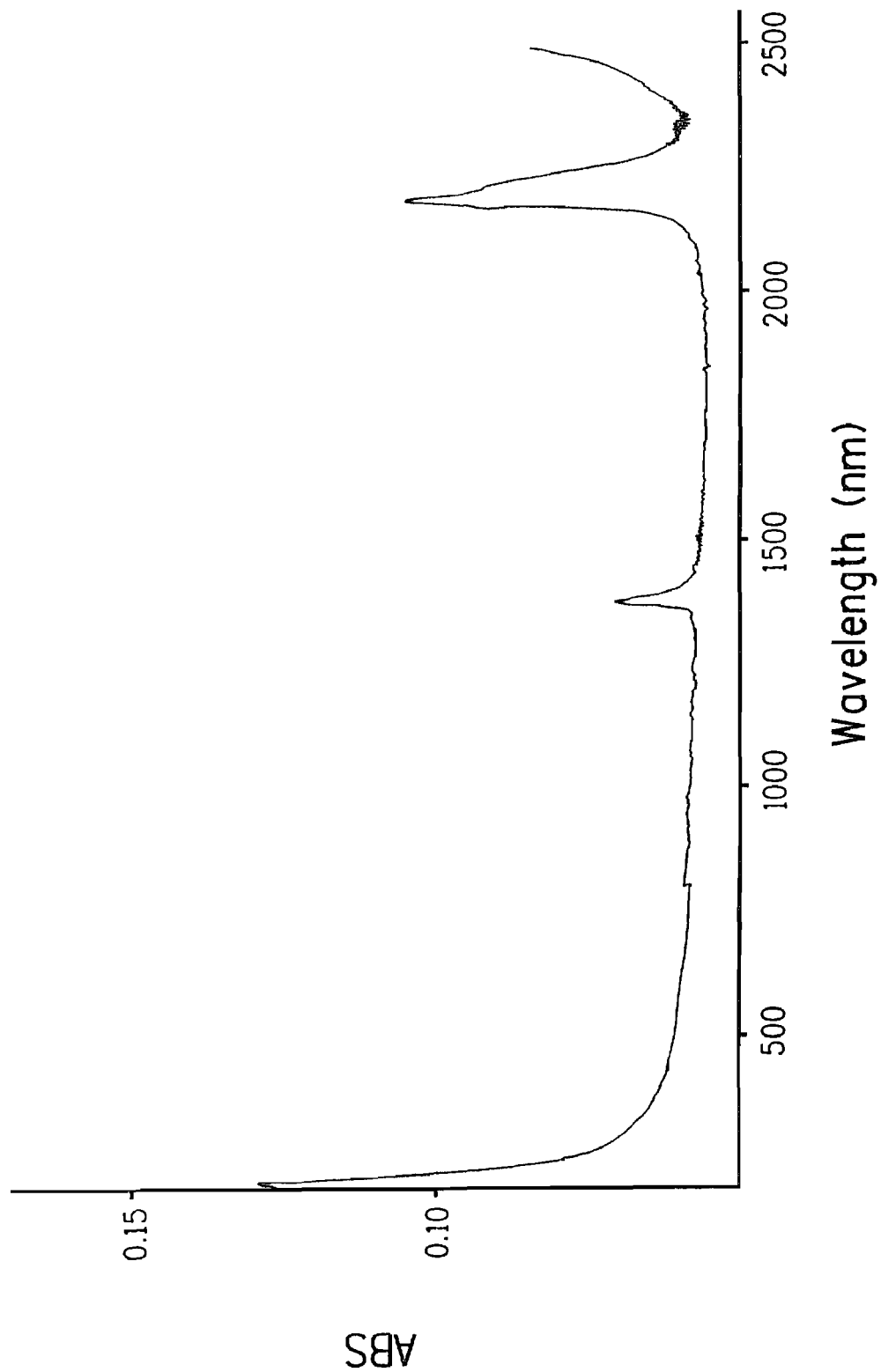
FIG. 3 shows the background NIR spectrum acquired for the evacuated sample cell as a blank.
Figure 4:
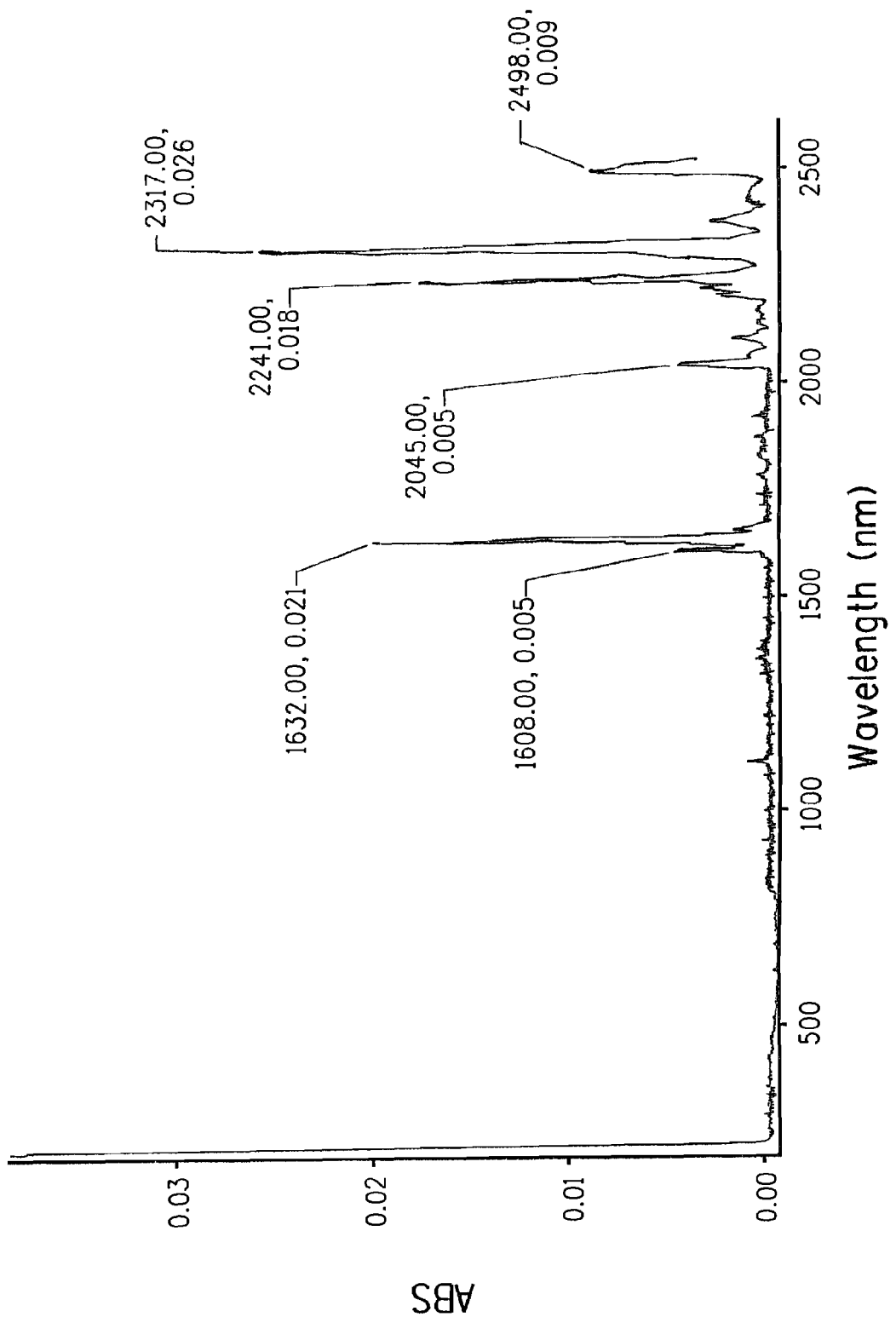
FIG. 4 shows the background subtracted NIR spectrum for HFC-1225ye.

This example demonstrates that a NIR spectrum can be obtained for a fluoroolefin as described herein. A sample of 1,2,3,3,3-pentafluoropropene (HFC-1225ye) was analyzed with a Varian Cary 500 UV/Vis/NIR spectrophotometer at ambient temperature. A 10 millimeter sample cell was charged with HFC-1225ye to a pressure of 748 torr on a vacuum line, having previously been evacuated. A background spectrum of the same evacuated (<1 mTorr) cell was acquired and subtracted from the sample spectrum. For both sample and background, points were acquired at 1 nanometer (nm) resolution and averaging 0.2 seconds per point, with a spectral bandwidth of 4 nm; the detector and grating changeover occurred at 800 nm and the UV source was activated at 350 nm; and the spectrum was scanned from 2600 to 190 nm. FIG. 2 shows the raw NIR spectral data for the HFC-1225ye sample. FIG. 3 shows the background NIR spectrum acquired for the evacuated sample cell. And FIG. 4 shows the background subtracted NIR spectrum for HFC-1225ye. These data verify that NIR spectra for fluoroolefins may be obtained that provide a unique fingerprint for detection of this class of compound.

What is claimed is:
1. A method of determining the components of a composition comprising a fluoroolefin in a fluid system, comprising sensing the components of the composition with sensing means for determining the identity of the components of the composition in the fluid system; wherein the sensing means comprises a NIR sensor that uses a light-emitting diode as the source of near infrared radiation.

2. The method of claim 1, further including sensing the components with the sensing means in order to determine the amount of the identified component.

3. The method of claim 1 or 2, wherein the sensing means senses the double bond structure of the fluoroolefin.

4. The method of claim 1, wherein the sensing means comprises an extraction device.

5. The method of claim 1, wherein the sensing means comprises a sensor mounted in-situ on a component in the system.

6. The method of claim 1, wherein the fluoroolefin comprises a compound having the formula E- or Z—$R^1$CH=CH$R^2$ (Formula I), wherein $R^1$ and $R^2$ are, independently, $C_1$ to $C_6$ perfluoroalkyl groups.

7. The method of claim 6, wherein the $R^1$ and $R^2$ groups are $CF_3$, $C_2F_5$, $CF_2CF_2CF_3$, $CF(CF_3)_2$, $CF_2CF_2CF_2CF_3$, $CF(CF_3)CF_2CF_3$, $CF_2CF(CF_3)_2$, $C(CF_3)_3$, $CF_2CF_2CF_2CF_2CF_3$, $CF_2CF_2CF(CF_3)^2$, $C(CF_3)_2C_2F_5$, $CF_2CF_2CF_2CF_2CF_2CF_3$, $CF(CF_3)CF_2CF_2C_2F_5$, and $C(CF_3)_2CF_2C_2F_5$.

8. The method of claim 1, wherein the fluoroolefin comprises a compound selected from the group consisting of $CF_3CF=CHF$, $CF_3CH=CF_2$, $CHF_2CF=CF_2$, $CHF_2CF=CHF$, $CF_3CF=CH_2$, $CF_3CH=CHF$, $CH_2FCF=CF_2$, $CHF_2CH=CF_2$, $CHF_2CF=CHF$, $CHF_2CF=CH_2$, $CF_3CH=CH_2$, $CH_3CF=CF_2$, $CH_2FCH=CF_2$, $CH_2FCF=CHF$, $CHF_2CH=CHF$, $CF_3CF=CFCF_3$, $CF_3CF_2CF=CF_2$, $CF_3CF=CHCF_3$, $CHF=CFCF_2CF_3$, $CHF_2CF=CFCF_3$, $(CF_3)_2C=CHF$, $CF_2=CHCF_2CF_3$, $CF_2=CFCHFCF_3$, $CF_2=CFCF_2CHF_2$, $CF_3CF_2CF=CH_2$, $CF_3CH=CHCF_3$, $CHF=CHCF_2CF_3$, $CHF=CFCHFCF_3$, $CHF=CFCF_2CHF_2$, $CHF_2CF=CFCHF_2$, $CH_2FCF=CFCF_3$, $CHF_2CH=CFCF_3$, $CF_3CH=CFCHF_2$, $CF_2=CFCF_2CH_2F$, $CF_2=CFCHFCHF_2$, $CH_2=C(CF_3)_2$, $CH_2FCH=CFCF_3$, $CF_3CH=CFCH_2F$, $CF_3CF_2CH=CH_2$, $CHF_2CH=CHCF_3$, $CF_3CF=CFCH_3$, $CH_2=CFCF_2CHF_2$, $CHF_2CF=CHCHF_2$, $CH_3CF_2CF=CF_2$, $CH_2FCF=CFCHF_2$, $CH_2FCF_2CF=CF_2$, $CF_2=C(CF_3)(CH_3)$, $CH_2=C(CHF_2)(CF_3)$, $CH_2=CHCF_2CHF_2$, $CF_2=C(CHF_2)(CH_3)$, $CHF=C(CF_3)(CH_3)$, $CH_2=C(CHF_2)_2$, $CF_3CF=CHCH_3$, $CH_2=CFCHFCF_3$, $CHF=CFCH_2CF_3$, $CHF=CHCHFCF_3$, $CHF=CHCF_2CHF_2$, $CHF=CFCHFCHF_2$, $CH_3CF=CHCF_3$, $CF_3CF=CFC_2F_5$, $CF_2=CFCF_2CF_2CF_3$, $(CF_3)_2C=CHCF_3$, $CF_3CF=CHCF_2CF_3$, $CF_3CH=CFCF_2CF_3$, $CHF=CFCF_2CF_2CF_3$, $CF_2=CHCF_2CF_2CF_3$, $CF_2=CFCF_2CF_2CHF_2$, $CHF_2CF=CFCF_2CF_3$, $CF_3CF=CFCF_2CHF_2$, $CF_3CF=CFCHFCF_3$, $CHF=CFCF(CF_3)_2$, $CF_2=CFCH(CF_3)_2$, $CF_3CH=C(CF_3)_2$, $CF_2=CHCF(CF_3)_2$, $CH_2=CFCF_2CF_2CF_3$, $CHF=CFCF_2CF_2CHF_2$, $CH_2=C(CF_3)CF_2CF_3$, $CF_2=CHCH(CF_3)_2$, $CHF=CHCF(CF_3)_2$, $CF_2=C(CF_3)CH_2CF_3$, $CF_3CF_2CF_2CH=CH_2$, $CH_2=CFCF_2CF_2CHF_2$, $CF_2=CHCF_2CH_2CF_3$, $CF_3CF=C(CF_3)(CH_3)$, $CH_2=CFCH(CF_3)_2$, $CHF=CHCH(CF_3)_2$, $CH_2FCH=C(CF_3)_2$, $CH_3CF=C(CF_3)_2$, $(CF_3)_2C=CHCH_3$, $C_2F_5CF=CHCH_3$, $CF_3C(CH_3)=CHCF_3$, $CH_2=CHCF_2CHFCF_3$, $CH_2=C(CF_3)CH_2CF_3$, $CF_3(CF_2)_3CF=CF_2$, $CF_3CF_2CF=CFCF_2CF_3$, $(CF_3)_2C=C(CF_3)_2$, $(CF_3)_2CFCF=CFCF_3$, $(CF_3)_2C=CHC_2F_5$, $(CF_3)_2CFCF=CHCF_3$, $CF_3CH=CHCF(CF_3)_2$, $CF_3CH=CHCF_2CF_3$, $CF_2CF_2CH=CHCF_2CF_3$, $CF_3CF_2CF_2CF_2CH=CH_2$, $CH_2=CHC(CF_3)_3$, $(CF_3)_2C=C(CH_3)(CF_3)$, $H_2=CFCF_2CH(CF_3)_2$, $CF_3CF=C(CH_3)CF_2CF_3$, $CF_3CH=CHCH(CF_3)_2$, $C_2F_5CF_2CF=CHCH_3$, $CH_2=CHCF_2CF_2CHF_2$, $(CF_3)_2C=CHCF_2CH_3$, $CH_2=C(CF_3)CH_2C_2F_5$, $CF_3CF_2CF_2C(CH_3)=CH_2$, $CF_3CF_2CF_2CH=CHCH_3$, $CH_2=CHCH_2CF_2C_2F_5$, $CF_3CF_2CF=CFC_2H_5$, $CH_2=CHCH_2CF(CF_3)_2$, $CF_3CF=CHCH(CF_3)(CH_3)$, $(CF_3)_2C=CFC_2H_5$, $CF_3CF=CFCF_2C_2F_5$, $CF_3CF_2CF=CFCF_2C_2F_5$, $CF_3CH=CFCF_2C_2F_5$, $CF_3CF=CHCF_2C_2F_5$, $CF_3CF_2CH=CFCF_2C_2F_5$, $CF_3CF_2CF=CHCF_2C_2F_5$, cyclo-$CF_2CF_2CF=CF—$, cyclo-$CF_2CF_2CH=CH—$, cyclo-$CF_2CF_2CF_2CH=CH—$, cyclo-$CF_2CF=CFCF_2CF_2—$, and cyclo-$CF_2CF=CFCF_2CF_2$.

9. The method of claim 2, further comprising recharging the components of the composition in response to the determination of the amount of the components of the composition.

10. The method of claim 1, wherein the composition comprising a fluoroolefin further comprises at least one compound selected from the group consisting of: HFC-1225ye, HFC-1234ze, HFC-1234yf, HFC-1234ye, HFC-1243zf, HFC-32, HFC-125, HFC-134, HFC-134a, HFC-143a, HFC-152a, HFC-161, HFC-227ea, HFC-236ea, HFC-236fa, HFC-245fa, HFC-365mfc, propane, n-butane, isobutane, 2-methylbutane, n-pentane, cyclopentane, dimethylether, $CF_3SCF_3$, $CO_2$, ammonia, and $CF_3I$.

11. A detection system for determining the components of a composition comprising a fluoroolefin in a fluid system, comprising means for sensing the double bond structure of a fluoroolefin in the fluid system; wherein the means for sensing the double bond structure comprises a NIR sensor sensor that uses a light-emitting diode as the source of near infrared radiation.

12. The detection system of claim 11, wherein the sensing means comprises an extraction device.

13. The method of claim 1, wherein the sensing means comprises a sensor mounted in-situ on a component in the system.

14. The detection system of claim 11, further including means for sensing the amount of each component in the composition.

15. The detection system of claim 14, further including a recovery line disposed between the system and a recovery tank for recharging the components of the fluoroolefin composition in response to the sensed amount of each component.

* * * * *